(12) United States Patent
Ohene-Frempong et al.

(10) Patent No.: US 11,380,444 B2
(45) Date of Patent: Jul. 5, 2022

(54) METHOD FOR IMPROVING HEALTH LITERACY OF PATIENT MATERIALS

(71) Applicant: Institute for Healthcare Advancement, La Habra, CA (US)

(72) Inventors: Janet Ohene-Frempong, Elkins Park, PA (US); Jann Keenan, Ellicott City, MD (US)

(73) Assignee: INSTITUTE FOR HEALTHCARE ADVANCEMENT, La Habra, CA (US)

( * ) Notice: Subject to any disclaimer, the term of this patent is extended or adjusted under 35 U.S.C. 154(b) by 0 days.

(21) Appl. No.: 16/528,373

(22) Filed: Jul. 31, 2019

(65) Prior Publication Data

US 2021/0035696 A1 Feb. 4, 2021

(51) Int. Cl.
| | | |
|---|---|---|
| *G16H 80/00* | (2018.01) | |
| *G16H 15/00* | (2018.01) | |
| *G16H 50/30* | (2018.01) | |
| *G06F 40/169* | (2020.01) | |
| *G06F 40/106* | (2020.01) | |

(52) U.S. Cl.
CPC ........... *G16H 80/00* (2018.01); *G06F 40/106* (2020.01); *G06F 40/169* (2020.01); *G16H 15/00* (2018.01); *G16H 50/30* (2018.01)

(58) Field of Classification Search
CPC ................................. G06F 17/00; G16H 80/00
See application file for complete search history.

(56) References Cited

U.S. PATENT DOCUMENTS

| | | | |
|---|---|---|---|
| 9,760,607 B1 | 9/2017 | Tweedy et al. | |
| 2008/0033751 A1* | 2/2008 | Greene | G06Q 50/00 |
| 2012/0310661 A1* | 12/2012 | Greene | G06Q 50/22 |
| 2014/0136236 A1* | 5/2014 | Lee | G06F 19/322 |
| 2015/0220697 A1* | 8/2015 | Hunt et al. | G06F 19/00 |
| 2016/0103875 A1 | 4/2016 | Zupancic | |
| 2017/0046311 A1 | 2/2017 | Walker | |
| 2017/0124268 A1* | 5/2017 | Zhang et al. | G06F 19/00 |

(Continued)

FOREIGN PATENT DOCUMENTS

| | | |
|---|---|---|
| JP | 2018-163660 A | 10/2018 |
| WO | 2021021820 A1 | 2/2021 |

OTHER PUBLICATIONS

International Search Report and Written Opinion; dated Nov. 11, 2020; issued in corresponding International Application No. PCT/US2020/043892, filed Jul. 28, 2020; 8 Pages.

*Primary Examiner* — James J Debrow
(74) *Attorney, Agent, or Firm* — Polsinell PC

(57) ABSTRACT

Systems, apparatus, and methods for improving health literacy of patient materials. The method includes receiving, from a communication source, a medical communication for a patient containing at least one of medical diagnostic information or medical treatment information. The method includes generating a health literacy assessment of the medical communication using at least one of a plurality of appearance metrics, a plurality of readability metrics, a plurality of document literacy metrics, or a plurality of quantitative literacy metrics. The method includes providing the health literacy assessment to the communication source to facilitate an improved conveyance of the at least one of the medical diagnostic information or the medical treatment information to increase comprehension by patients of all educational levels.

20 Claims, 19 Drawing Sheets

(56) References Cited

U.S. PATENT DOCUMENTS

| | | | |
|---|---|---|---|
| 2017/0161439 A1* | 6/2017 | Raduchel et al. | G06F 19/322 |
| 2018/0239873 A1* | 8/2018 | Eda et al. | G06F 19/3418 |
| 2021/0020281 A1* | 1/2021 | Castine et al. | G06F 16/35 |
| 2021/0065908 A1* | 3/2021 | Qwnby et al. | G16H 50/30 |

* cited by examiner

| Plurality of Metrics Appearance | | | |
|---|---|---|---|
| | Work Needed | | |
| Makes information LOOK easy to read. (SPACING, CONTRAST, AND TYPOGRAPHY) | Much | Some | None or little |
| Paragraph depth and chunking of information<br>☐ Depth: Keeps paragraphs short. (Ideal: 4 to 5 lines, if possible)<br>☐ Grouping or chunking Breaks longer information into logical groups or chunks. | | | |
| Line length<br>☐ Keeps length of lines to about 5 inches across. | | | |
| White space<br>☐ Provides ample white space to provide visual relief. | | | |
| Front size<br>☐ Ideally, uses a 12-point Times New Roman equivalent or larger for readers who may have poor vision. | | | |
| Font style and case<br>☐ For hard copy: Uses either serif or sans serif font for hard copy.<br>☐ For Web: Uses sans serif for Web copy.<br>☐ Reverse type: Limits reverse type. (light type on a dark background)<br>☐ Italics: Limits the use of italics.<br>☐ All CAPS: Limits the use of all UPPERCASE lettering<br>☐ Number of fonts: Limits number of fonts per piece. | | | |
| Leading (line spacing)<br>☐ Chooses line spacing of 1.5 if space allows. | | | |
| Contrast<br>☐ Provides sharp contrast between background and copy. (Black is preferable to dark gray, if budget allows) | | | |
| Background<br>☐ Ghosting: Avoids ghosting. (placing text on top of shaded backgrounds, photos, or patterns)<br>☐ Superimposition: Avoids placing text on top of illustrations. | | | |

FIG. 6A

| Plurality of Metrics Appearance | | | |
|---|---|---|---|
| | Work Needed | | |
| | Much | Some | None or little |
| 621 — Makes information easy to FIND and FOLLOW. (ORGANIZATION AND LAYOUT) | | | |
| 623 — Headings, subheadings, and short titles<br>☐ Uses bolded or enlarged headings and subheadings to highlight the key messages and make information easy to find and follow.<br>☐ Uses a short sentence, a phrase or a single word. | | | |
| 625 — Vertical lists with bullets, letters, and numbers<br>☐ Are used, when needed: Breaks dense text into vertical lists to limit concept density and to make information easier to find.<br>☐ Number of items is limited: Limits the number of items or concepts on a list to no more than 7.<br>☐ Uses grouping or chunking, when needed: Breaks longer lists into logical groups or chunks to avoid overwhelming the reader.<br>☐ Uses parallel structure: Lists items using parallel structure (same grammatical form). For example, all verbs or all nouns<br>☐ Uses alphabet, when appropriate: Uses alphabetical order, if needed, when items or topics are of equal importance.<br>☐ Uses numerical order, when needed - Uses numbers when items or steps need to be presented in a particular sequence.<br>☐ Allows the single bullet: To provide consistency, it is allowed within a larger list, when only one point is being made. | | | |
| 627 — Indentation<br>☐ Uses indentation to visually call attention to sub-points. | | | |
| 629 — Margins and alignment<br>☐ Uses a left justified margin to show readers where to begin.<br>☐ Uses a ragged right margin to help readers find and keep their place from one line to the next.<br>☐ Avoids full justification to eliminate potentially confusing gaps.<br>☐ Only uses centering for short blocks of text, if needed | | | |
| 631 — Boxing and callouts<br>☐ Uses boxing, if needed, to draw attention to key messages. | | | |

FIG. 6B

| Plurality of Metrics Appearance | | | |
|---|---|---|---|
| | Work Needed | | |
| Makes information easy to FIND and FOLLOW. (ORGANIZATION AND LAYOUT) | Much | Some | None or little |
| Uninterrupted copy and wrapping of text<br>☐ Keeps readers from having to follow a word, a sentence or a message from one column to the next, or from one page to the next.<br>　Keeps similar info on the same page or on a 2-page spread, if possible.<br>☐ Avoids end-of-line hyphens.<br>☐ Is free of widows, orphans, and "misfits".<br>☐ Avoids wrapped text. | | | |
| Tables of contents<br>☐ Keeps titles in the tables of contents short and immediately informative, and matches them with the headers on the pages that follow. (For longer documents)<br>☐ Provides usable information to guide the reader.<br>☐ Organizes the table into categories or chunks, with bolded headers and sub-headers, if the table of contents is lengthy. | | | |
| Numbering of pages<br>☐ Numbers pages to guide the reader and help providers to counsel consumers.<br>☐ Labels page bottoms so that they can serve as advance organizers, if document is lengthy. (12 pages or longer) | | | |
| Section indicators (for reader instructions)<br>☐ Uses clear section headers or parts. (For longer documents) | | | |
| Color coding<br>☐ Any color coding is done in a consistent, non-confusing way. | | | |

FIG. 6C

| Plurality of Metrics Appearance | | | |
|---|---|---|---|
| | Work Needed | | |
| Makes information LOOK interesting and clear. (GRAPHICS and ILLUSTRATIONS) | Much | Some | None or little |
| Graphic usefulness<br>☐ Uses graphics that contribute to the message in any of the following ways:<br>– Attract attention.<br>– Indicate who the material is for.<br>– Increase comprehension of the text.<br>– Support the main messages.<br>– Motivate or inspire the reader to take the intended action. | | | |
| Use of realistic graphics<br>☐ In general, uses realistic graphics that would indicate what the information is about, even in the absence of the relevant copy - and even to people who may not be familiar with the topic.<br>☐ Sparingly uses or carefully explains metaphorical imaging that may be misinterpreted by literal readers. | | | |
| Clarity and simplicity of graphics<br>☐ Illustrations are readily recognizable.<br>☐ Does not include unnecessary background or extraneous details.<br>☐ Places graphics next to the related copy. | | | |
| Anatomical illustrations and microscopic views<br>☐ Presents any internal parts of the body in context of the rest of the body.<br>☐ Avoids or carefully explains any microscopic views. | | | |
| Captions and cueing<br>☐ Uses captions to clarify the main point of a graphic.<br>☐ Uses explicit directional cues to call attention to parts of a graphic. (For example, arrows or generally recognized symbols with brief captions) | | | |
| Depiction of unwanted behaviors<br>☐ Avoids inadvertently promoting unwanted behaviors. | | | |

FIG. 6D

| Plurality of Metrics Readability | | | |
|---|---|---|---|
| | \multicolumn{3}{c}{Work Needed} | | |
| Makes information easy to READ (TEXT) | Much | Some | None or little |
| Document length and complexity<br>For shorter documents (a 1 to 6-page document):<br>☐ Keeps the content simple.<br>☐ Skips the "nice-to-know" details and focuses on the "need-to-know information".<br><br>For longer documents (a document with more than 6 pages)<br>☐ If needed, creates another section for the "nice-to-know information". | | | |
| Word length<br>☐ Keeps words short, when possible. (Ideal: fewer than 3 syllables) | | | |
| Word pronunciation guides<br>☐ Provides pronunciation guides, when needed. | | | |
| Sentence length<br>☐ Keeps sentences short, when possible. (Ideal: less than 10 to 15 words).<br>☐ Attempts to vary the sentence length to create an engaging rhythm and maintain reader attention. | | | |
| Reading level<br>Meets grade reading level requirements (4th to 6th grade for marginal readers) without:<br>☐ making information inaccurate<br>☐ making information confusing<br>☐ Making the flow of information seem choppy or childish | | | |

FIG. 7A

| Plurality of Metrics Readability | | | |
|---|---|---|---|
| | Work Needed | | |
| Makes information easy to READ (TEXT) | Much | Some | None or little |
| Clarity of purpose<br>☐ Provides a useful title and introductory text that makes it clear what the material is about. | | | |
| Background information<br>☐ Provides background information, if needed, to help the lay reader to better grasp the information being presented. | | | |
| Sequence of information<br>☐ Seems to consider reader priorities, then presents information in an order that is likely to make sense to the intended reader. | | | |
| Informative and scannable headers<br>☐ Uses descriptive headers and sub-headers to break the information into manageable sections that can be easily understood and scanned for the main messages. | | | |
| Directives or calls to action<br>☐ Are clear and explicit: Makes calls-to-action explicit and clear, not implied. (Don't smoke vs. You should not smoke)<br>☐ Use verbs: Begins directives with VERBS.<br>☐ Get to the point: Quickly gets to the point and tells people what to DO, if they want to achieve a specific desired result. Then, nicely explains why and, if needed, how to do so.<br>☐ Put key calls to action first. Does not visually embed them deep in the document. | | | |
| Active voice for statements<br>☐ Uses the active voice for statements, if possible. For example, say "We made and error", instead of "An error was made". | | | |
| Abbreviations, acronyms, phone words, and symbols<br>☐ Avoids or explains abbreviations, acronyms, and symbols.<br>☐ Provides the accompanying numerals when using phonewords. | | | |

FIG. 7B

| Plurality of Metrics Readability | | | |
|---|---|---|---|
| | colspan Work Needed | | |
| Makes information easy to UNDERSTAND. (TEXT) | Much | Some | None or little |
| Word clarity<br>☐ Potentially confusing words: Avoids or explains the meaning of words likely to cause confusion. This includes:<br>— professional jargon (renal vs. kidney) - medical, legal, social service, or insurance terminology<br>— value judgment words (a lot of rest vs. 8 hours of sleep each night)<br>— category words (poultry vs. chicken)<br>— concept words (self-esteem vs. the way you feel about yourself)<br>— idioms (feel under the weather vs. don't feel well)<br>☐ Familiar term as the lead: Makes the technical term parenthetical, when needed. [For example: salt (sodium)]<br>☐ Different terms with the same meaning: Points out the potential confusion when different words or terms mean or refer to the same thing (For example: Affordable Care Act, ACA, and Obamacare, or SNAP and Food Stamps)<br>☐ Consistent use or terms: Uses a word or term consistently throughout the document. | | | |
| Glossaries<br>☐ Provides an easy-to-read glossary, if needed.<br>— Tries to define or explain technical or medical terms when they appear, whenever possible.<br>— Keeps definitions simple and tests them with marginal readers in the intended audience.<br>— Provides explanations, in addition to definitions, to make implied messages explicit for readers who are unfamiliar with a term and the issues that surround it.<br>For example:<br>(Consumer Directed Health Plan - a potential euphemism) | | | |

FIG. 7C

| Plurality of Metrics Readabiltiy | | | |
|---|---|---|---|
| | Work Needed | | |
| Makes information easy to UNDERSTAND. (TEXT) | Much | Some | None or little |
| Questions and answers<br>☐ Answers any question posed promptly and clearly, before going into any other detail. | | | |
| Parallel construction for contrasting and comparing<br>☐ Uses parallel construction (repeated wording and layout) when there is a need to easily contrast and compare two or more sections of information. (For example, when comparing different health plans in order to choose one) | | | |
| Limited cross referencing<br>☐ Limits the need for the reader to search around for related information. (see page such and such) | | | |
| Summaries and reviews<br>☐ Summarizes key points and offers reviews for new information or for long documents. | | | |

FIG. 7D

| Plurality of Metrics Readability | | | |
|---|---|---|---|
| | \multicolumn{3}{c}{Work Needed} | | |
| Makes information easy to RELATE TO. (TEXT) | Much | Some | None or little |
| Reader-focused content and reader appeal<br>☐ Seems to address the key concerns and interests of the lay readership.<br>☐ Seems to address information on a way that intended readers will perceive the materials as being:<br>— interesting, important, needed, timely<br>— practical (easy to respond to)<br>— acceptable (not offensive in any way)<br>— believable or persuasive<br>— personally relevant (meant especially for them) | | | |
| A conversational style<br>☐ Addresses the reader directly. ("your heart" vs. "the heart")<br>☐ Uses "living room language": familiar terms and the active voice. | | | |
| A narrative approach<br>When appropriate, effectively uses one or more of the follow techniques to make the information even easier to engage with, believe, accept, and/or relate to as being personally relevant to the reader. This includes culturally sensitive, non-stigmatizing:<br>☐ storylines<br>☐ dialogues<br>☐ testimonials<br>☐ quotes | | | |
| An opportunity for interaction<br>When appropriate, uses one or more of the following approaches to invite interaction, engage the reader with the copy, and encourage deeper thought:<br>☐ A helpful checklist<br>☐ A brief but relevant quiz<br>☐ Questions and answers about misconceptions or controversies<br>☐ Fill in the blank | | | |

FIG. 7E

| Plurality of Metrics Readability | | | |
|---|---|---|---|
| | Work Needed | | |
| BREAKS SELECTED GRAMMAR and STYLE RULES (to make information easier to read and understand) | Much | Some | None or little |
| Beginning sentences with a conjunction<br>☐ When needed, begins with a CONJUNCTION to shorten sentences and to maintain a conversational tone.<br>Source:<br>http://www.chicagomanualofstyle.org/qanda/data/faq/ topics/Usage/faq0013.html | | | |
| Ending sentences with a preposition<br>☐ When needed, ends with a PREPOSITION to make sentences easier to understand and maintain a conversational tone.<br>Source:<br>http://www.chicagomanualofstyle.org/qanda/data/faq/ topics/Prepositions.html | | | |
| Using a serial comma (an Oxford comma)<br>☐ When a conjunction joins the last two elements in a series of three or more, a comma appears before the conjunction. Chicago strongly recommends this widely practiced usage since it prevents ambiguity.<br>Source:<br>http://www.chicagomanualofstyle.org/16/ch06/ch06_sec018. html?sessionId=dd0f6bd3-6aa4-45f2-8556-7479858f9412 | | | |
| Using numerals for numbers instead of, or in addition to, using words<br>☐ Uses NUMERALS instead of WORDS, even for numbers one (1) through ten (10) to make them easier to spot and grasp in the body of text - especially when noting the number seems like it would be crucial to the reader (For example: Send this form back within ten (10) days).<br>Sources:<br>http://www.printwand.com/blog/using-numbers-in-writing-tips-for-your-print-marketing<br>http://www.nngroup.com/articles/web-writing-show- numbers-as-numerals/ | | | |

FIG. 7F

| Plurality of Document Literacy Metrics | | | |
|---|---|---|---|
| | \multicolumn{3}{c}{Work Needed} | | |
| Makes non-continuous text easy to understand and use. ("Document Literacy" Issues) | Much | Some | None or little |
| Forms and diaries<br>For the introduction<br>☐ Purpose: Explains why the document is important and what to do with it.<br>☐ Directions: Provides clear directions.<br>☐ Sample entries: Provides sample entries, when possible.<br>For the body<br>☐ Font size: Uses a large enough font size, when possible.<br>☐ Entries: The document is simple and requires a limited number of entries, when possible.<br>☐ Shading: Uses light shading or white space to distinguish One line or section from the next.<br>☐ Space: Provides adequate space for writing in requested information.<br>☐ Writing: Limits the amount of writing required. | | | |
| Charts and tables<br>☐ Columns: Keeps charts simple by limiting the number of columns.<br>☐ Labels: Provides clear labels that explicitly indicate what each column or row (axis) means.<br>☐ Arrows: Uses arrows, if needed, to show readers how to navigate the x-y axis orientation of the table.<br>☐ Writing: Limits the amount of writing.<br>☐ Color coding: Uses color coding or light shading to distinguish one row or column from the other. | | | |

FIG. 8A

| Plurality of Document Literacy Metrics | | | |
|---|---|---|---|
| Makes non-continuous text easy to understand and use. ("Document Literacy" Issues) | Work Needed | | |
| | Much | Some | None or little |
| Graphs<br>☐ Interprets information for lay readers.<br>☐ Uses laymen's terms. | | | |
| Maps<br>☐ Considers design issues that make information easy to see and read, such as:<br>– adequate font type and size<br>– adequate contrast<br>☐ Makes special map-related issues easy to follow such as:<br>– placement of map key<br>– N-S-E-W orientation<br>– symbols (such as male and female restroom icons)<br>– arrows to indicate directions and destinations<br>– color coding<br>☐ Offers information on whom to contact for verbal guidance. | | | |

FIG. 8B

| Plurality of Quantitative Literacy Metrics | | | |
|---|---|---|---|
| | Work Needed | | |
| Makes numbers meaningful. ("Quantitative Literacy" Issues) | Much | Some | None or little |
| Limited use<br>☐ Limits the use of numbers.<br>☐ Focuses on just a few concepts.<br>☐ Uses numbers when precision is needed. (blood sugar, dose of medicine) | | | |
| Plain language explanations<br>☐ Explains the meaning of specific numbers with everyday words, when needed. ("49 percent" or "about half") | | | |
| Calculations<br>☐ Does the math for the reader, when possible. Does not expect reader to perform calculations.<br>☐ Performs sample calculations when reader-specific calculations are not possible. | | | |
| Visuals<br>☐ Provides pictures to help explain numerical concepts, when needed. | | | |
| Analogies and comparisons<br>☐ Uses analogies and comparisons to familiar objects to help convey quantitative information. | | | |

FIG. 9A

| Plurality of Quantitative Literacy Metrics | | | |
|---|---|---|---|
| | \multicolumn{3}{c}{Work Needed} | | |
| | Much | Some | None or little |
| Makes numbers clear.<br>("Quantitative Literacy" Issues) | | | |
| Providing estimates<br>☐ Elaborates by providing estimated numbers. | | | |
| Using frequencies<br>☐ Uses frequencies instead of decimals or percentages. | | | |
| Using different measurement systems<br>☐ Uses the measurement system that the readers use.<br>(the U.S. Customary System or the metric system). | | | |
| Framing outcomes<br>☐ Frames outcomes in both positive and negative terms. | | | |
| Consistency when making comparisons<br>☐ Keeps denominators and timeframes the same when comparing numbers. | | | |

FIG. 9B

METHOD FOR IMPROVING HEALTH LITERACY OF PATIENT MATERIALS

BACKGROUND

1. Field of the Invention

This specification relates to systems, apparatus, and methods for improving health literacy of patient materials.

2. Description of the Related Art

One of the most common and most easily fixed impediments to a person's overall health revolves around their ability to comprehend health educational materials (i.e. health literacy). Health literacy is defined as the degree to which a person has the capacity to obtain, process, and understand basic health information and services needed to make appropriate health decisions. Increasingly, patients are receiving wellness information, diagnosis information, and/or medical treatment information from their physician not in person but via e-mail, secure message, or letter. The information contained in those medical communications is frequently laden with difficult to understand terminology and guidance that confuses a vast number of patients.

The lack of face-to-face interaction at the time of these medical communications compound the above-mentioned problem and make it inherently less likely for the patient to follow recommended treatments or reach out to the physician for additional information, clarification, or explanations. These compounded issues put the patient at a high risk for developing future health problems or escalating the severity of existing health problems. For example, if a patient who has been recently diagnosed with diabetes does not fully understand what the negative consequences their extended inaction would bring, they are likely to continue their inaction. As a result, the patient may face a worsening of their symptoms as well as possible amputation(s), loss of vision, or death as a result of their inaction.

When these issues are coupled with the reality that most people don't receive regular health examinations or check-ups, it should come as no surprise that medical conditions go untreated or unmitigated for extended periods of time and ineffective treatments are continuously used. Moreover, the more a patient understands the contents of the medical communication the more likely they are to take an active role in their own treatment. If the nature of the treatment is fully understood by the patient, the patient is more likely to recognize the signs that the treatment is effective and more likely to recognize the signs that the treatment is ineffective. This leads to a more effective treatment because the patient is more likely to have the knowledge to recognize when the treatment is ineffective and report it accordingly to the supervising physician.

SUMMARY

In general, one aspect of the subject matter described in this specification may be embodied in a method for improving health literacy of patient materials. The method includes receiving, from a communication source, a medical communication for a patient containing at least one of medical diagnostic information or medical treatment information. The method includes generating a health literacy assessment of the medical communication using at least one of a plurality of appearance metrics, a plurality of readability metrics, a plurality of document literacy metrics, or a plurality of quantitative literacy metrics. The method includes providing the health literacy assessment to the communication source to facilitate an improved conveyance of the at least one of the medical diagnostic information or the medical treatment information to increase comprehension by patients of all educational levels.

These and other embodiments may optionally include one or more of the following features. The method may include receiving, from the communication source, a new medical communication based on the provided health literacy assessment and containing the at least one of medical diagnostic information or medical treatment information.

The plurality of appearance metrics may include at least two of paragraph length, paragraph grouping, line length, amount of white space, font size, font style and case, line spacing, contrast, background, presence of headings, subheadings, and short titles, presence of vertical lists with at least one of bullets, letters, or numbers, indentation, margins, and alignment, usage of boxing and callouts, uninterrupted text, usage of a table of contents, numbering of pages, presence of section indicators, presence of color coding, usage of graphics, usage of realistic graphics, clarity and simplicity of graphics, usage of anatomical illustrations and microscopic views, usage of captions and cueing, or depiction of unwanted behaviors. The plurality of appearance metrics may be based on a first set of predetermined parameters.

The plurality of readability metrics may include at least two of text length and complexity, word length, usage of word pronunciation guides, sentence length, reading level, clarity of purpose, usage of background information, sequence of information, usage of informative and scannable headers, usage of directives and calls to action, usage of active voice for statements, presence of abbreviations, acronyms, phone words, and symbols, word clarity, usage of glossaries, presence of answers to questions, usage of parallel construction for contrasting and comparing, usage of cross referencing, usage of summaries and reviews, usage of reader-focused content and reader appeal, usage of conversational style, usage of narrative approach, presence of an opportunity for interaction, usage of conjunctions at the beginning of sentences, usage of prepositions at the end of sentences, usage of an Oxford comma, or usage of numerals for numbers. The plurality of readability metrics may be based on a second set of predetermined parameters.

The plurality of document literacy metrics may include at least one of usage of forms and diaries, usage of charts and tables, usage of graphs, or usage of maps. The plurality of document literacy metrics may be based on a third set of predetermined parameters. The plurality of quantitative literacy metrics may include at least one of usage of numbers, usage of plain language explanations, usage of calculations, usage of visuals, usage of analogies and comparisons, usage of estimates, usage of frequencies, usage of measurement systems, presence of framing of outcomes, or consistency when making comparisons. The plurality of quantitative literacy metrics may be based on a fourth set of predetermined parameters.

In another aspect, the subject matter may be embodied in an apparatus for improving health literacy of patient materials. The apparatus includes a memory configured to store an assessment application corresponding to a reviewer. The apparatus includes a network access device configured to receive a medical communication, from a communication source, containing at least one of medical diagnostic information or medical treatment information. The apparatus includes one or more processors configured to perform operations of the assessment application. The operations include generating a health literacy assessment of the medical communication using at least one of a plurality of appearance metrics, a plurality of readability metrics, a plurality of document literacy metrics, or a plurality of quantitative literacy metrics. The apparatus includes an output device configured to output the health literacy assessment to facilitate an improved conveyance of the at least one of the medical diagnostic information or the medical treatment information to increase comprehension by patients of all educational levels.

In another aspect, the subject matter may be embodied in a method for generating a score for patient materials to improve health literacy. The method includes storing, in a memory, an assessment application. The method includes receiving, from a network access device, a medical communication containing at least one of medical diagnostic information or medical treatment information. The method includes generating, using one or more processors and the assessment application, a score of the medical communication based on at least one of a plurality of appearance metrics, a plurality of readability metrics, a plurality of document literacy metrics, or a plurality of quantitative literacy metrics. The method includes outputting, using an output device, the score to facilitate an improved conveyance of the at least one of the medical diagnostic information or the medical treatment information to increase comprehension by patients of all educational levels.

BRIEF DESCRIPTION OF THE DRAWINGS

The features and advantages of the embodiments of the present disclosure will become more apparent from the detailed description set forth below when taken in conjunction with the drawings. Naturally, the drawings and their associated descriptions illustrate example arrangements within the scope of the claims and do not limit the scope of the claims. Reference numbers are reused throughout the drawings to indicate correspondence between referenced elements.

FIGS. 6A-6D show an example plurality of appearance metrics according to an aspect of the present disclosure.

FIGS. 7A-7F show an example plurality of readability metrics according to an aspect of the present disclosure.

FIGS. 8A-8B show an example plurality of document literacy metrics according to an aspect of the present disclosure.

FIGS. 9A-9B show an example plurality of quantitative literacy metrics according to an aspect of the present disclosure.

DETAILED DESCRIPTION

Figure 1:
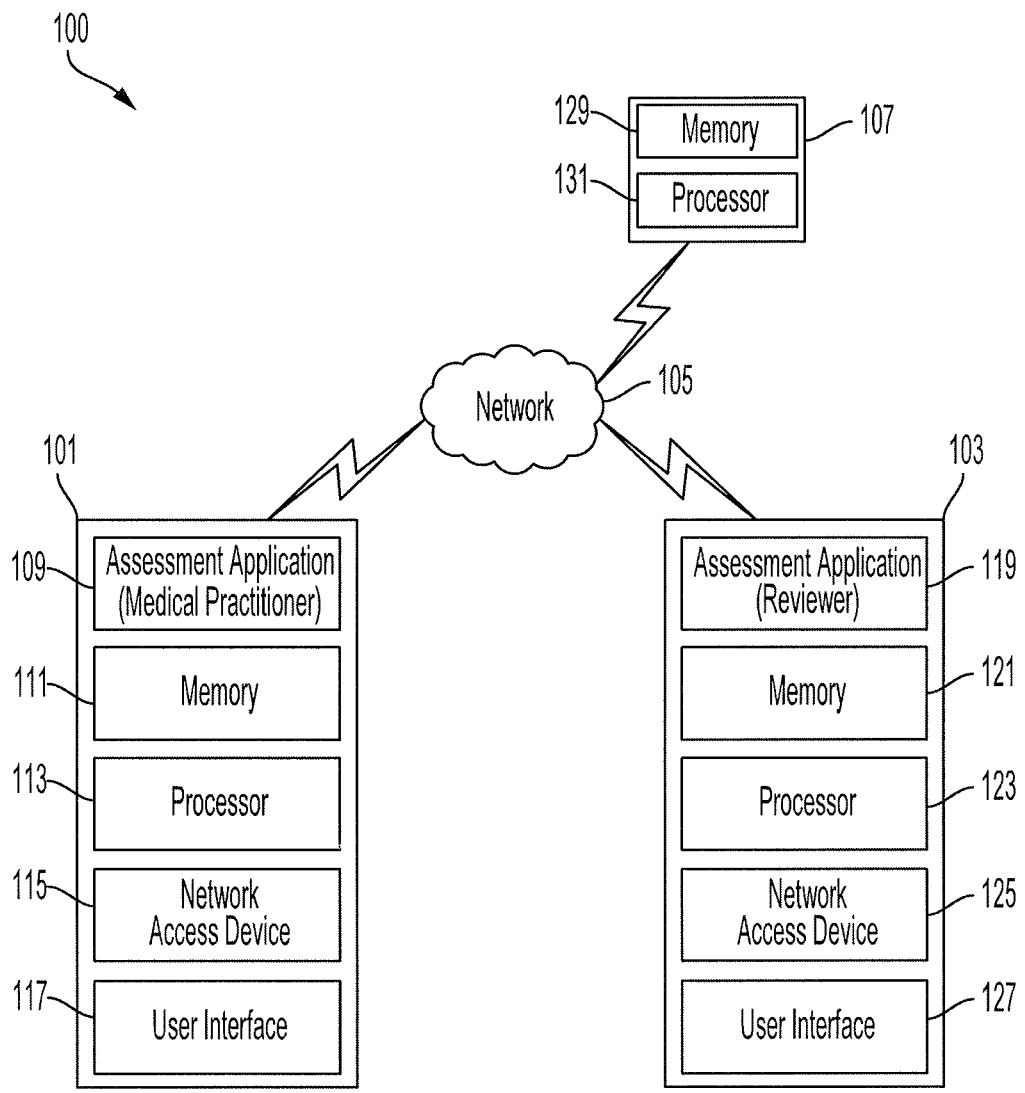
FIG. 1 shows a health literacy system for improving health literacy of patient materials according to an aspect of the present disclosure.

In the following detailed description, numerous specific details are set forth to provide an understanding of the present disclosure. It will be apparent, however, to one of ordinarily skilled in the art that elements of the present disclosure may be practiced without some of these specific details. In other instances, well-known structures and techniques have not been shown in detail to avoid unnecessarily obscuring the present disclosure.

Prior attempts to improve comprehension of health education materials (i.e. health literacy) have centered around providing seminars to healthcare personnel. The seminars provide insight and techniques in using simpler language and providing information at a lower educational level. However, the implementation of these techniques may not be monitored, and the healthcare personnel may continue to use complicated language and provide information at much higher educational levels than advised. Additionally, healthcare personnel may initially use simpler language but may, after time, revert back to using more complicated language. While these seminars may provide illustrative examples for the healthcare personnel, they do not offer a way to continuously and consistently assess medical communications to improve health literacy of patient materials.

The systems, apparatus, and methods for improving health literacy of patient materials, as described herein, may generate a health literacy assessment of a medical communication, received from a communication source, in order to provide an improved conveyance of at least one of medical diagnostic information or medical treatment information to increase comprehension by patients of all educational levels. The conveyance of the at least one of the medical diagnostic information or the medical treatment information may be improved through simplifying, organizing, or shortening the contents of the medical communication using the health literacy assessment. By improving the conveyance of the above-mentioned information, the patient is more likely to understand the contents of the medical communication and follow the guidance of the medical practitioner.

This, in turn, reduces the likelihood of the patient developing a future disease or worsening of the symptoms of a current disease. For example, if a patient is notified that they have been diagnosed with pre-diabetes and that they need to monitor and maintain a healthy blood sugar level, they may not grasp the severity of the situation. Consequently, the patient may not follow the guidance of the medical practitioner. If instead, they are told that they are developing a condition that could have lifelong consequences but could be reversed if they engage in exercise and eat a diet low in sugar and carbohydrates, the patient is much more likely to follow these recommended guidelines.

By understanding the contents of the medical communication, the patient is also more likely to take a more active role in their own treatment, which increases the likelihood of an improvement in the patient's treatment. For example, if a patient receives a medical communication indicating that they have been diagnosed with gestational diabetes and the patient's only additional takeaway is that they need to take a daily insulin injection, then the patient may face future medical issues. More specifically, by being unaware that by continuously eating foods laden with carbohydrates, their blood sugar may surpass healthy limits and could cause permanent damage to the baby. If, however, the patient understands that in addition to taking daily insulin injections they must also limit their daily carbohydrate intake, then they are more likely to keep their blood sugar within healthy limits, ignore contrary advice to eat carbohydrates, and thus reduce the likelihood of causing undue damage to the baby.

FIG. 1 shows a health literacy system 100. The health literacy system 100 includes a communication source computing device 101 associated with a communication source and a reviewer computing device 103 associated with a reviewer. The communication source may be at least one of a physician, surgeon, specialist, nurse, therapist, psychiatrist, psychologist, medical assistant, pharmacist, technician, dietitian, medical technologist, clerk, or staff member. The communication source may be associated with at least one of a physician's office, drug company, medical device company, non-profit organization, or medical clinic, and may generate a communication such as a medical communication. According to various implementations, the communication source may be associated with various hospitals, group practices, medical clinics, non-profit organizations, or healthcare organizations interchangeably. The reviewer may be associated with at least one of a physician's office, drug company, medical device company, non-profit organization, medical clinic, or may be separate from the association of the communication source. According to various implementations, the reviewer may be associated with various hospitals, group practices, medical clinics, non-profit organizations, or healthcare organizations interchangeably.

Figure 5:
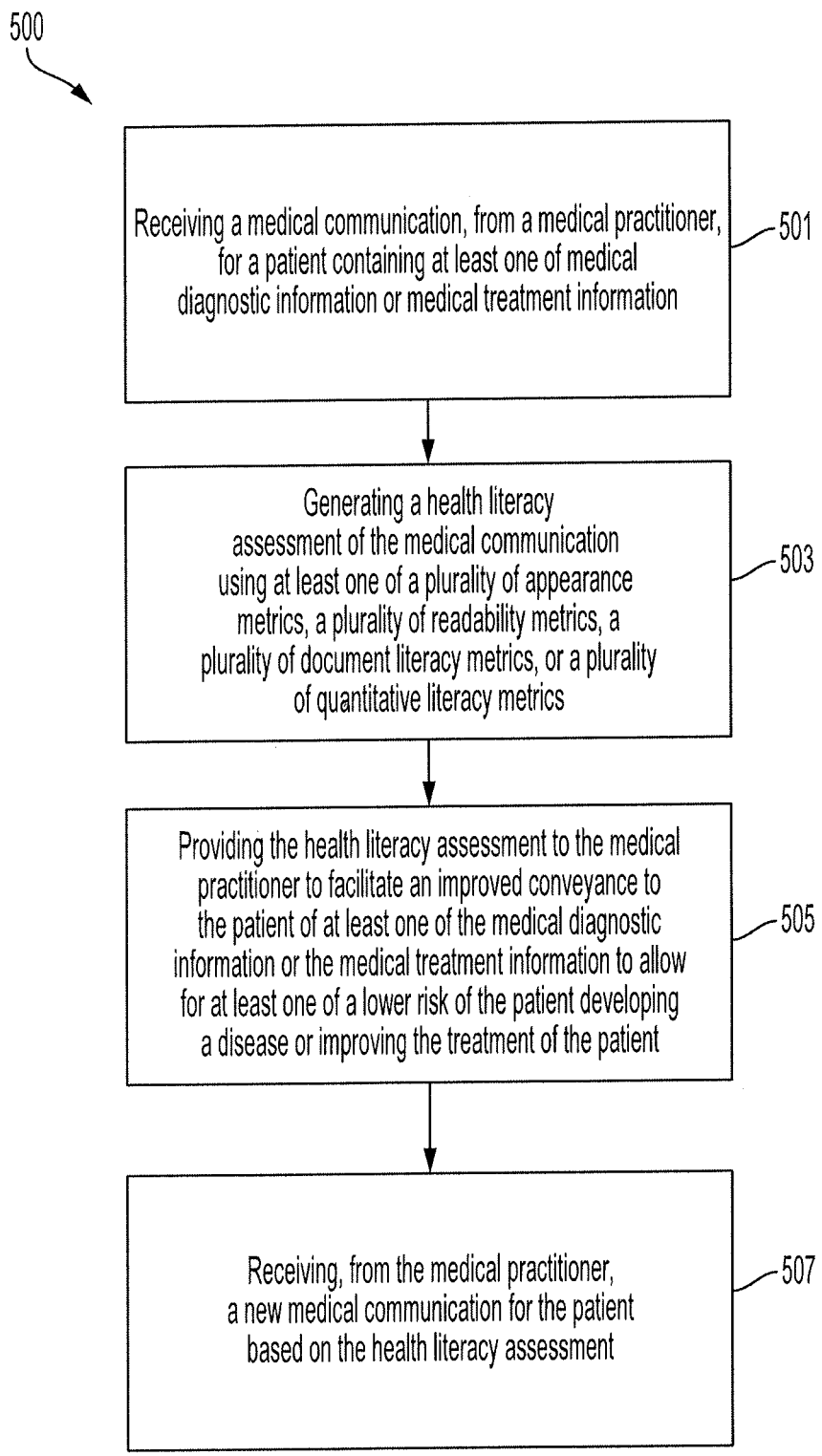
FIG. 5 is a flow diagram of a process for improving health literacy of patient materials according to an aspect of the present disclosure.

The health literacy system 100 may perform the process 500 shown in FIG. 5. The reviewer may be tasked with generating a health literacy assessment of the medical communication. The health literacy system 100 may include at least one of a network 105 or a server 107. The server 107 may have a memory 129 and a processor 131. In some implementations, the server 107 may be protected by a firewall in order to protect sensitive information communicated with the server 107 and stored thereon. For example, a patient's medical records or data related to the patient's medical treatment may be protected by the firewall. The different components, such as the communication source computing device 101, the reviewer computing device 103, and the server 107 may communicate with each other through the network 105.

The health literacy system 100 includes the communication source computing device 101. The communication source computing device 101 may have an assessment application 109 loaded on the communication source computing device 101. The assessment application 109 may be used to create a medical communication. In some implementations, the communication source computing device 101 may download the assessment application 109 from the server 107. The communication source computing device 101 includes a memory 111, a processor 113, and a network access device 115. The assessment application 109 may have or use a user interface 117 that receives input from a user, such as a communication source.

The assessment application 109 may be stored in the memory 111. The memory 111 may store instructions to execute on the processor 113 and may include one or more of a RAM or other volatile or non-volatile memory. The memory 111 may be a non-transitory memory or a data storage device, such as a hard disk drive, a solid-state drive, a hybrid disk drive, or other appropriate data storage, and may further store machine-readable instructions, which may be loaded and executed by the processor 113. The memory 111 may be encrypted in order to protect sensitive information stored thereon. For example, a patient's medical records or data related to the patient's medical treatment may be encrypted.

The assessment application 109 may at least one of include, interface, or interact with a user interface 117. The user interface 117 may include any device capable of receiving user input, such as a button, a dial, a microphone, a graphical user interface or a touch screen, and any device capable of output, such as a display, a speaker, a refreshable braille display, or a combination device such as a touch screen. The user interface 117 allows a user (e.g. a communication source) to communicate with the assessment application 109. For example, the user (e.g. the communication source) may be able to provide data to the assessment application 109 such as a medical document, and/or receive feedback from the assessment application 109 via the user interface 117. A medical communication for a patient may be prepared using the assessment application 109. The medical communication may contain at least one of medical diagnostic information or medical treatment information related to the patient. For example, the medical communication may contain information related to a diagnosis of diabetes. In another example, the medical communication may contain information regarding insulin therapy for the treatment of diabetes. In some implementations, the assessment application 109 may send the medical communication to the reviewer computing device 103.

The network access device 115 may include a communication port or channel, such as one or more of a Wi-Fi unit, a Bluetooth® unit, a radio frequency identification (RFID) tag or reader, or a cellular network unit for accessing a cellular network (such as 3G or 4G). The assessment application 109 may communicate with at least one of the reviewer computing device 103 or the server 107 through the network 105. The network 105, such as Bluetooth Low Energy (BLE) network, a local area network (LAN), a wide area network (WAN), a cellular network, the Internet, or combination thereof, connects the communication source computing device 101 to at least one of the reviewer computing device 103 or the server 107.

The health literacy system 100 includes the reviewer computing device 103. The reviewer computing device 103 may have an assessment application 119 loaded on the reviewer computing device 103. The assessment application 119 may be used to generate a health literacy assessment of the medical communication. In some implementations, the reviewer computing device 103 may download the assessment application 119 from the server 107 or may access the assessment application 119 from the server. The reviewer computing device 103 includes a memory 121, a processor 123, and a network access device 125. The assessment application 119 may have or use a user interface 127 that receives input from a user, such as a reviewer. In some implementations, the reviewer computing device 103 may include an output device.

In some implementations, the assessment application 119 and the assessment application 109 may be the same application. In other implementations, the assessment application 119 may be a specialized application for reviewers and the assessment application 109 may be a specialized application for communication sources. The assessment application 119 may be used by a reviewer to generate a health literacy assessment of the medical communication after receiving the medical communication from the communication source. The generated health literacy assessment may be outputted by the output device. In some implementations, the output device may be at least one of the user interface 127 on the reviewer computing device 103 or the user interface 117 on the communication source computing device 101.

The assessment application 119 may be stored in the memory 121. The memory 121 may store instructions to execute on the processor 123 and may include one or more of a RAM or other volatile or non-volatile memory. The memory 121 may be a non-transitory memory or a data storage device, such as a hard disk drive, a solid-state disk drive, a hybrid disk drive, or other appropriate data storage, and may further store machine-readable instructions, which may be loaded and executed by the processor 123. The memory 121 may be encrypted in order to protect sensitive information stored thereon. For example, a patient's medical records or data related to the patient's medical treatment may be encrypted.

The assessment application 119 may at least one of include, interface or interact with a user interface 127. The user interface 127 may include any device capable of receiving user input, such as a button, a dial, a microphone, a graphical user interface or a touch screen, and any device capable of output, e.g., a display, a speaker, a refreshable braille display, or a combination such as a touchscreen. The user interface 127 allows a user (e.g. a reviewer) to communicate with the assessment application 119. For example, the user (e.g. the reviewer) may be able to provide data to the assessment application 119 such as user input, and/or receive feedback from the assessment application 119 via the user interface 127.

The network access device 125 may include a communication port or channel, such as one or more of a Wi-Fi unit, a Bluetooth® unit, a radio frequency identification (RFID) tag or reader, or a cellular network unit for accessing a cellular network (such as 3G or 4G). The assessment application 119 may communicate with at least one of the communication source computing device 101 or the server 107 through the network 105. The network 105, such as Bluetooth Low Energy (BLE) network, a local area network (LAN), a wide area network (WAN), a cellular network, the Internet, or combination thereof, connects at least one of the reviewer computing device 103 to the communication source computing device 101 or the server 107.

In some implementations, the assessment application 119 may generate and output the health literacy assessment to the communication source after the medical communication has been received by the reviewer computing device 103 from the communication source computing device 101. The health literacy assessment may be generated near-instantaneously. For example, the health literacy assessment may be generated in a matter of seconds. Human beings are incapable of performing the health literacy assessment in a matter of seconds. In some implementations, the reviewer may perform the process 500 shown in FIG. 5 using the assessment application 119.

Figure 2:
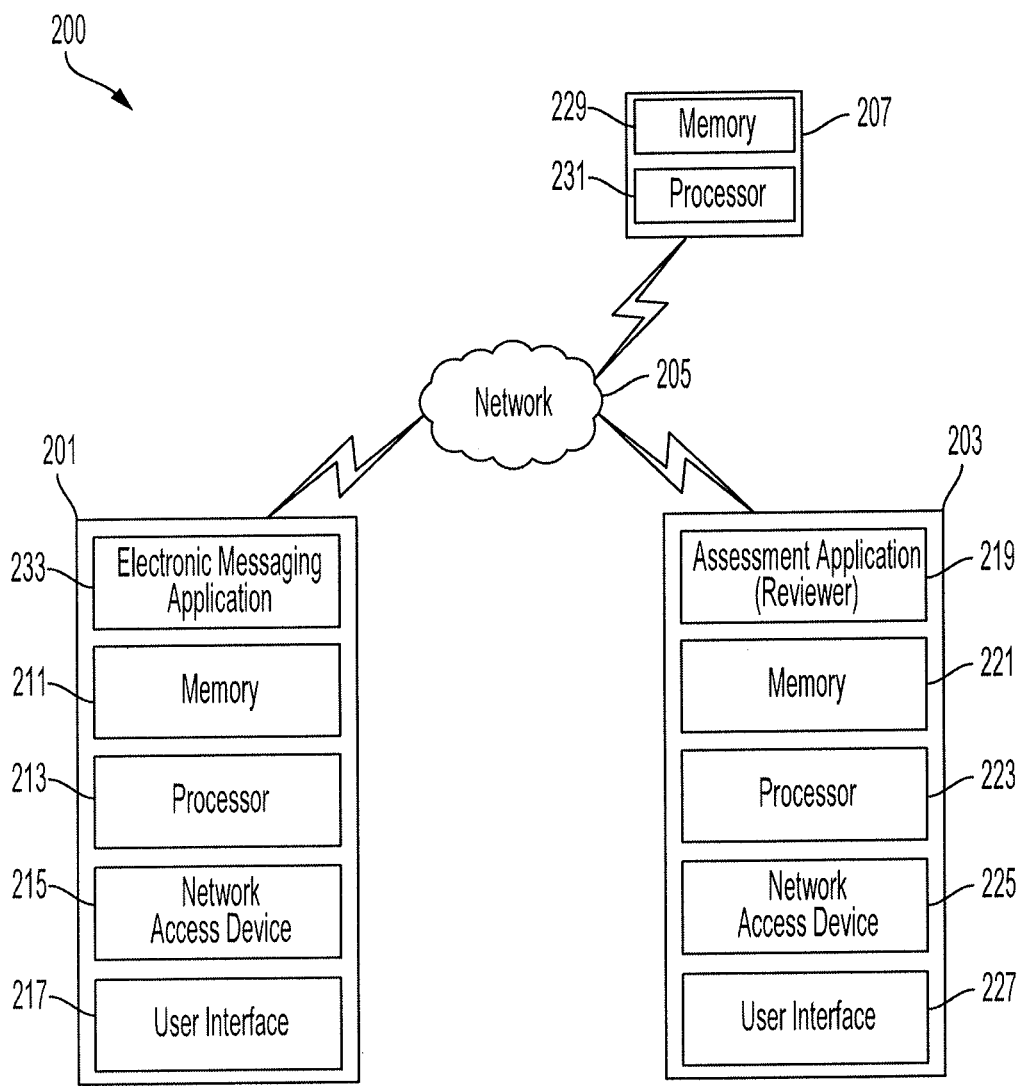
FIG. 2 shows a health literacy system for improving health literacy of patient materials according to an aspect of the present disclosure.

FIG. 2 shows a health literacy system 200. The health literacy system 200 includes a communication source computing device 201 associated with a communication source and a reviewer computing device 203 associated with a reviewer. The health literacy system 200 is similar to the health literacy system 100, and like parts are numbered similarly. The health literacy system 200 may perform the process 500 shown in FIG. 5.

The health literacy system 200 may include at least one of a network 205 or a server 207. The network 205 may be configured similarly as the network 105 discussed in regard to FIG. 1, and may include similar features as the network 105 discussed in regard to FIG. 1. The server 207 may be configured similarly as the server 107 discussed in regard to FIG. 1, and may include similar features as the server 107 discussed in regard to FIG. 1.

The health literacy system 200 includes the communication source computing device 201. The communication source computing device 201 may have an electronic messaging application 233 loaded on the communication source computing device 201. The communication source computing device 201 includes a memory 211, a processor 213, and a network access device 215. The electronic messaging application 233 may have or use a user interface 217 that receives input from a user, such as a communication source.

The memory 211 may be configured similarly as the memory 111 discussed in regard to FIG. 1, and may include similar features as the memory 111 discussed in regard to FIG. 1. The processor 213 may be configured similarly as the processor 113 discussed in regard to FIG. 1, and may include similar features as the processor 113 discussed in regard to FIG. 1. The network access device 215 may be configured similarly as the network access device 115 discussed in regard to FIG. 1, and may include similar features as the network access device 115 discussed in regard to FIG. 1. The user interface 217 may be configured similarly as the user interface 117 discussed in regard to FIG. 1, and may include similar features as the user interface 117 discussed in regard to FIG. 1.

A medical communication for a patient may be prepared using the electronic messaging application 233. The medical communication may contain at least one of medical diagnostic information or medical treatment information related to the patient. In some implementations, the electronic messaging application 233 may send the medical communication to the reviewer computing device 203.

The health literacy system 200 includes the reviewer computing device 203. The reviewer computing device 203 may be configured similarly as the reviewer computing device 103 discussed in regard to FIG. 1, and may include similar features as the reviewer computing device 103 discussed in regard to FIG. 1.

In some implementations, the assessment application 219 may generate and provide a health literacy assessment to the communication source after the medical communication has been received by the reviewer computing device 203 from the communication source computing device 201. The health literacy assessment may be generated near-instantaneously. For example, the health literacy assessment may be generated in a matter of seconds. Human beings are incapable of performing the health literacy assessment in a matter of seconds. In other implementations, the reviewer may perform the process 500 shown in FIG. 5 using the assessment application 219.

Figure 3:
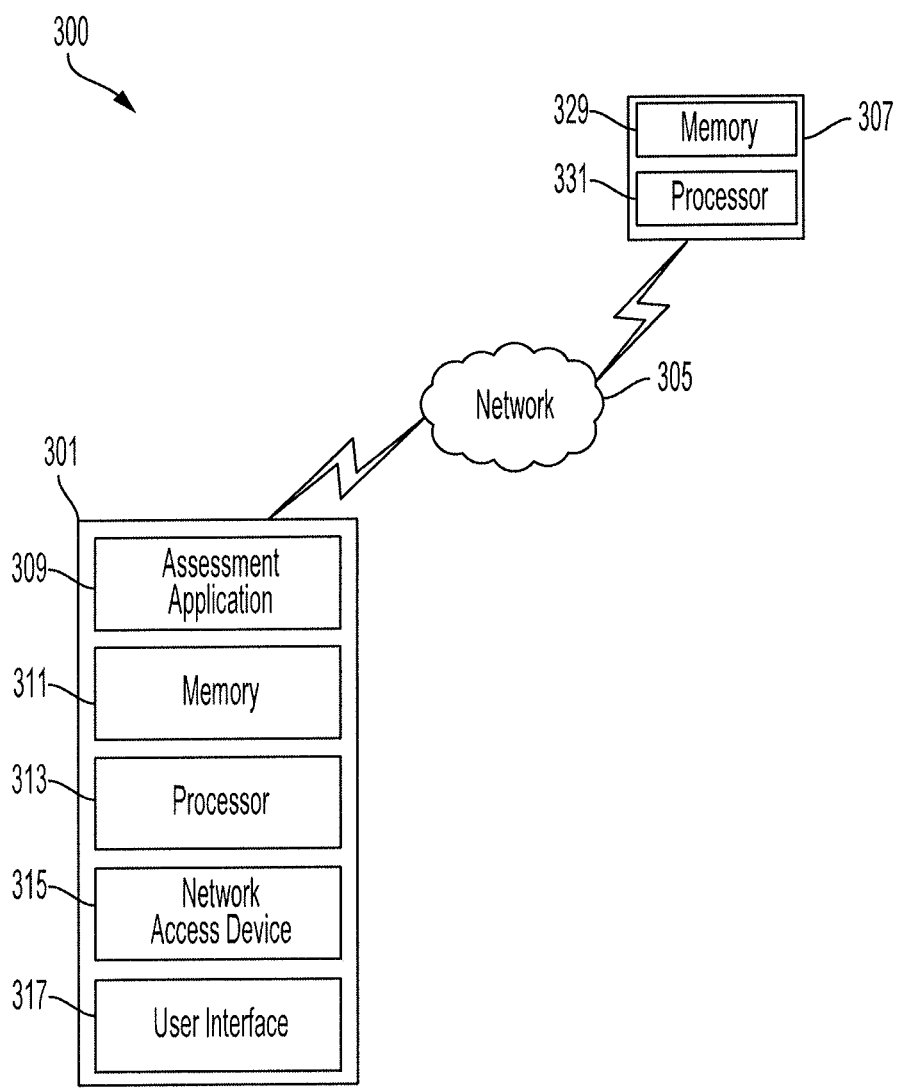
FIG. 3 shows a health literacy system for improving health literacy of patient materials according to an aspect of the present disclosure.

FIG. 3 shows a health literacy system 300. The health literacy system 300 includes a communication source computing device 301 associated with a communication source. The health literacy system 300 is similar to the health literacy systems 100 and 200, and like parts are numbered similarly.

The health literacy system 300 may include at least one of a network 305 or a server 307. The network 305 may be configured similarly as the network 105, 205 discussed in regard to FIGS. 1-2, and may include similar features as the network 105, 205 discussed in regard to FIGS. 1-2. The server 307 may be configured similarly as the server 107, 207 discussed in regard to FIGS. 1-2, and may include similar features as the server 107, 207 discussed in regard to FIGS. 1-2.

The health literacy system 300 includes the communication source computing device 301. The communication source computing device 301 includes an assessment application 309, a memory 311, a processor 313, and a network access device 315. The assessment application 309 may have or use a user interface 317 that receives input from a user, such as a communication source. In some implementations, the communication source computing device 301 may include an output device.

In some implementations, the assessment application 309 may be located on the server 307. The assessment application 309 may be stored in the memory 329 of the server 307. The communication source computing device 301 may access the assessment application 309 stored on the server 307 via the network 305 using the network access device 315.

The health literacy system 300 may perform the process 500 shown in FIG. 5. The memory 311 may be configured similarly as the memory 111, 211 discussed in regard to FIGS. 1-2, and may include similar features as the memory 111, 211 discussed in regard to FIGS. 1-2. The processor 313 may be configured similarly as the processor 113, 213 discussed in regard to FIGS. 1-2, and may include similar features as the processor 113, 213 discussed in regard to FIGS. 1-2. The network access device 315 may be configured similarly as the network access device 115, 215 discussed in regard to FIGS. 1-2, and may include similar features as the network access device 115, 215 discussed in regard to FIGS. 1-2. The user interface 317 may be configured similarly as the user interface 117, 217 discussed in regard to FIGS. 1-2, and may include similar features as the user interface 117, 217 discussed in regard to FIGS. 1-2.

A medical communication for a patient may be prepared using the assessment application 309. The medical communication may contain at least one of medical diagnostic information or medical treatment information related to the patient. In some implementations, the assessment application 309 may perform the process 500 shown in FIG. 5. The assessment application 309 may automatically generate and provide a health literacy assessment to the communication source as the medical communication is being prepared. For example, the health literacy assessment may be generated in real-time. Human beings are incapable of performing the health literacy assessment in real-time. The generated health literacy assessment may be outputted by the output device. In some implementations, the output device may be the user interface 317.

In other implementations, the assessment application 309 may generate and provide a health literacy assessment to the communication source after the medical communication has been prepared. The health literacy assessment may be generated near-instantaneously. For example, the health literacy assessment may be generated in a matter of seconds. Human beings are incapable of performing the health literacy assessment in a matter of seconds.

Figure 4:
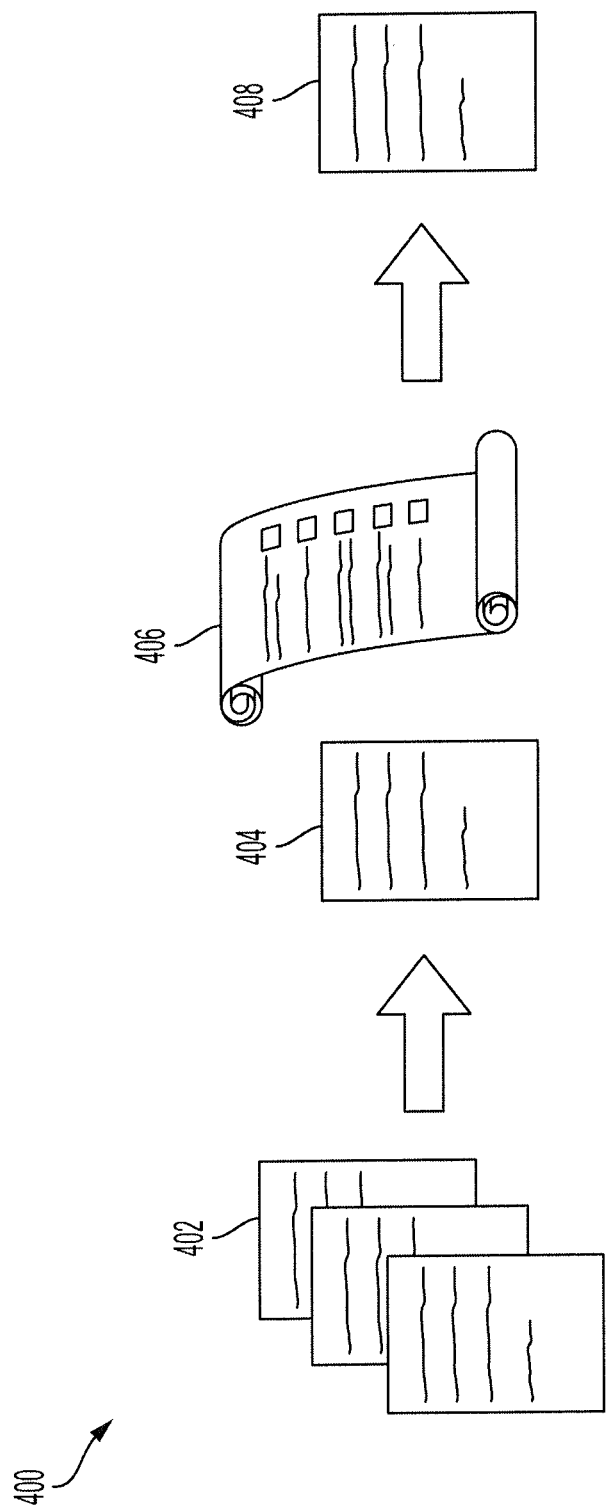
FIG. 4 shows a process flow of a method for improving health literacy of patient materials according to an aspect of the present disclosure.

FIG. 4 shows a process flow 400 of a method for improving health literacy of patient materials. According to various embodiments, the method may be the process 500 shown in FIG. 5. A medical communication 402 for a patient containing at least one of medical diagnostic information or medical treatment information related to the patient may be received from a communication source by a human reviewer (reviewer). The medical communication may be in the form of at least one of a hard (paper) document or an electronic document.

The reviewer may first read the medical communication 402. The reviewer may then generate a health literacy assessment 404 of the medical communication 402 using at least one of a plurality of appearance metrics corresponding to FIGS. 6A-6D, a plurality of readability metrics corresponding to FIGS. 7A-7F, a plurality of document literacy metrics corresponding to FIGS. 8A-8B, or a plurality of quantitative literacy metrics 406 corresponding to FIGS. 9A-9B. The at least one of the plurality of appearance metrics, the plurality of readability metrics, the plurality of document literacy metrics, or the plurality of quantitative literacy metrics 406 may be listed in the form of at least one of a hard (paper) document or an electronic document. The reviewer may generate a health literacy assessment 404 by writing down, using a hard (paper document), or by entering, using an electronic document, scores of the at least one of the plurality of appearance metrics, the plurality of readability metrics, the plurality of document literacy metrics, or the plurality of quantitative literacy metrics.

The reviewer may provide the completed health literacy assessment 408 to the communication source to facilitate an improved conveyance of at least one of the medical diagnostic information or the medical treatment information to increase comprehension by patients of all educational levels. The conveyance of the at least one of the medical diagnostic information or the medical treatment information may be improved through simplifying, organizing, or shortening the contents of the medical communication using the health literacy assessment 408. The health literacy assessment 404 provided to the communication source may be in the form of a hard (paper) document or an electronic document. For example, the reviewer may score the medical communication using a document similar to those shown in FIGS. 6A-6D, 7A-7F, 8A-8B, and 9A-9B.

FIG. 5 is a flow diagram of a process 500 that may be implemented by the systems 100, 200, 300 discussed in regard to FIGS. 1-3 and the process flow 400 discussed in regard to FIG. 4.

A medical communication for a patient containing at least one of medical diagnostic information or medical treatment information may be received from a communication source (501). The medical communication may be received by the assessment application 119, 219 on the reviewer computing device 103, 203 (as shown in FIGS. 1-2). The medical communication may be received by the assessment application 309 on the communication source computing device 301 (as shown in FIG. 3). The medical communication may be received by a human reviewer (reviewer) (as shown in FIG. 4).

The medical communication may be prepared by the communication source using the assessment application 109, 309 on the communication source computing device 101, 301 (as shown in FIGS. 1 and 3). The medical communication may be prepared by the communication source using the electronic messaging application 233 on the communication source computing device 201 (as shown in FIG. 2). The medical communication may be prepared by the communication source using a hard (paper) document or an electronic document (as shown in FIG. 4).

The medical communication may be in the form of at least one of an e-mail, text message, secure message, or letter. The medical communication may be a communication for a patient regarding medical advice, medical outlook, medical test results, medical treatment recommendations, medical treatment instructions, medical diagnosis, physician appointments, medical test appointments, prescription information, or wellness information.

A health literacy assessment of the medical communication may be generated using at least one of a plurality of appearance metrics, a plurality of readability metrics, a plurality of document literacy metrics, or a plurality of quantitative literacy metrics (503). The health literacy assessment may be generated by a reviewer using the assessment application 119, 219 on the reviewer computing device 103, 203 (as shown in FIGS. 1-2). The health literacy assessment may be generated by the assessment application 119, 219 on the reviewer computing device 103, 203 (as shown in FIGS. 1-2). The health literacy assessment may be generated by the assessment application 309 on the communication source computing device 301 (as shown in FIG. 3). The health literacy assessment may be generated by a human reviewer (reviewer) (as shown in FIG. 4).

The generated health literacy assessment may be in the form of a grading of the medical communication, made by the reviewer, of the at least one of the plurality of appearance metrics, the plurality of readability metrics, the plurality of document literacy metrics, or the plurality of quantitative literacy metrics. For example, the medical communication may receive a grading of some work needed for one or more metrics within the plurality of appearance metrics, a grading of much work needed for one or more metrics within the plurality of readability metrics, and a grading of none or little work needed for one or more metrics within the plurality of document literacy metrics.

The generated health literacy assessment may be in the form of a grading of the medical communication in addition to notes explaining the grading and/or offering suggestions to improve the grading, made by the reviewer, of the at least one of the plurality of appearance metrics, the plurality of readability metrics, the plurality of document literacy metrics, or the plurality of quantitative literacy metrics. For example, the medical communication may receive a grading of some work needed for one or more metrics within the plurality of appearance metrics, a grading of much work needed for one or more metrics within the plurality of readability metrics, and a grading of none or little work needed for one or more metrics within the plurality of document literacy metrics. Each of the aforementioned gradings may include notes explaining each gradings and/or offering suggestions to improve each grading for the medical communication.

In some implementations, the generated health literacy assessment may be in the form of a grading of the medical communication, made by the assessment application 119, 219, 309, of the at least one of the plurality of appearance metrics, the plurality of readability metrics, the plurality of document literacy metrics, or the plurality of quantitative literacy metrics. For example, the medical communication may receive a grading of some work needed for one or more metrics within the plurality of appearance metrics, a grading of much work needed for one or more metrics within the plurality of readability metrics, and a grading of none or little work needed for one or more metrics within the plurality of document literacy metrics.

In some implementations, the generated health literacy assessment may be in the form of a grading of the medical communication in addition to notes explaining the grading and/or offering suggestions to improve the grading, made by the assessment application 119, 219, 309, of the at least one of the plurality of appearance metrics, the plurality of readability metrics, the plurality of document literacy metrics, or the plurality of quantitative literacy metrics. For example, the medical communication may receive a grading of some work needed for one or more metrics within the plurality of appearance metrics, a grading of much work needed for one or more metrics within the plurality of readability metrics, and a grading of none or little work needed for one or more metrics within the plurality of document literacy metrics. Each of the aforementioned gradings may include notes explaining each gradings and/or offering suggestions to improve each grading for the medical communication.

In some implementations, the at least one of the plurality of appearance metrics, the plurality of readability metrics, the plurality of document literacy metrics, or the plurality of quantitative literacy metrics may be stored in the assessment application 119, 219 on the reviewer computing device 103, 203 (as shown in FIGS. 1-2). In other implementations, the at least one of the plurality of appearance metrics, the plurality of readability metrics, the plurality of document literacy metrics, or the plurality of quantitative literacy metrics may be stored in the memory 121, 221 on the reviewer computing device 103, 203 (as shown in FIGS. 1-2).

In some implementations, the at least one of the plurality of appearance metrics, the plurality of readability metrics, the plurality of document literacy metrics, or the plurality of quantitative literacy metrics may be stored in the assessment application 309 on the medical practitioner computing device 301 (as shown in FIG. 3). In other implementations, the at least one of the plurality of appearance metrics, the plurality of readability metrics, the plurality of document literacy metrics, or the plurality of quantitative literacy metrics may be stored in the memory 311 on the medical practitioner computing device 301 (as shown in FIG. 3). The at least one of the plurality of appearance metrics, the plurality of readability metrics, the plurality of document literacy metrics, or the plurality of quantitative literacy metrics may be stored in the form of a hard (paper) document or an electronic document (as shown in FIG. 4).

The plurality of appearance metrics may include at least one, two, or more of paragraph length, paragraph grouping, line length, amount of white space, font size, font style and case, line spacing, contrast, background, presence of headings, subheadings, and short titles, presence of vertical lists with at least one of bullets, letters, or numbers, indentation, margins, and alignment, usage of boxing and callouts, uninterrupted text, usage of a table of contents, numbering of pages, presence of section indicators, presence of color coding, usage of graphics, usage of realistic graphics, clarity and simplicity of graphics, usage of anatomical illustrations and microscopic views, usage of captions and cueing, or depiction of unwanted behaviors (as shown in FIGS. 6A-6D). In some implementations, the plurality of appearance metrics may be based on a first set of predetermined parameters. The first set of predetermined parameters may be at least one of numerical values, guidelines, upper boundaries, lower boundaries, or other evaluation criteria for each metric within the plurality of appearance metrics.

The first set of predetermined parameters may be stored in the assessment application 119, 219 on the reviewer computing device 103, 203 (as shown in FIGS. 1-2). The first set of predetermined parameters may be stored in the memory 121, 221 on the reviewer computing device 103, 203 (as shown in FIGS. 1-2). The first set of predetermined parameters may be stored in the assessment application 309 on the communication source computing device 301 (as shown in FIG. 3). The first set of predetermined parameters may be stored in the memory 311 on the communication source computing device 301 (as shown in FIG. 3). The first set of predetermined parameters may be stored in the form of a hard (paper) document or an electronic document (as shown in FIG. 4).

In some implementations, the assessment application 119, 219, 309 may transform the contents of the medical communication to fit within the first set of predetermined parameters. For example, the assessment application 119, 219, 309 may transform the font size, font style, and case of the text within the medical communication to fit within the first set of predetermined parameters.

The plurality of readability metrics may include at least one, two, or more of length and complexity, word length, usage of word pronunciation guides, sentence length, reading level, clarity of purpose, usage of background information, sequence of information, usage of informative and scannable headers, usage of directives and calls to action, usage of active voice for statements, presence of abbreviations, acronyms, phone words, and symbols, word clarity, usage of glossaries, presence of answers to questions, usage of parallel construction for contrasting and comparing, usage of cross referencing, usage of summaries and reviews, usage of reader-focused content and reader appeal, usage of conversational style, usage of narrative approach, presence of an opportunity for interaction, usage of conjunctions at the beginning of sentences, usage of prepositions at the end of sentences, usage of an Oxford comma, or usage of numerals for numbers (as shown in FIGS. 7A-7F). In some implementations, the plurality of readability metrics may be based on a second set of predetermined parameters. The second set of predetermined parameters may be at least one of numerical values, guidelines, upper boundaries, lower boundaries, or other evaluation criteria for each metric within the plurality of readability metrics.

The second set of predetermined parameters may be stored in the assessment application 119, 219 on the reviewer computing device 103, 203 (as shown in FIGS. 1-2). The second set of predetermined parameters may be stored in the memory 121, 221 on the reviewer computing device 103, 203 (as shown in FIGS. 1-2). The second set of predetermined parameters may be stored in the assessment application 309 on the communication source computing device 301 (as shown in FIG. 3). The second set of predetermined parameters may be stored in the memory 311 on the communication source computing device 301 (as shown in FIG. 3). The second set of predetermined parameters may be stored in the form of a hard (paper) document or an electronic document (as shown in FIG. 4).

In some implementations, the assessment application 119, 219, 309 may transform the contents of the medical communication to fit within the second set of predetermined parameters. For example, the assessment application 119, 219, 309 may scan the medical communication for difficult to pronounce words and add word pronunciation guides for the difficult to pronounce words to the medical communication.

The plurality of document literacy metrics may include at least one of usage of forms and diaries, usage of charts and tables, usage of graphs, or usage of maps (as shown in FIGS. 8A-8B). In some implementations, the plurality of document literacy metrics may be based on a third set of predetermined parameters. The third set of predetermined parameters may be at least one of numerical values, guidelines, upper boundaries, lower boundaries, or other evaluation criteria for each metric within the plurality of document literacy metrics.

The third set of predetermined parameters may be stored in the assessment application 119, 219 on the reviewer computing device 103, 203 (as shown in FIGS. 1-2). The third set of predetermined parameters may be stored in the memory 121, 221 on the reviewer computing device 103, 203 (as shown in FIGS. 1-2). The third set of predetermined parameters may be stored in the assessment application 309 on the communication source computing device 301 (as shown in FIG. 3). The third set of predetermined parameters may be stored in the memory 311 on the communication source computing device 301 (as shown in FIG. 3). The third set of predetermined parameters may be stored in the form of a hard (paper) document or an electronic document (as shown in FIG. 4).

In some implementations, the assessment application 119, 219, 309 may transform the contents of the medical communication to fit within the third set of predetermined parameters. For example, the assessment application 119, 219, 309 may compile information within the medical communication into a table.

The plurality of quantitative literacy metrics may include at least one, two, or more of usage of numbers, usage of plain language explanations, usage of calculations, usage of visuals, usage of analogies and comparisons, usage of estimates, usage of frequencies, usage of measurement systems, presence of framing of outcomes, or consistency when making comparisons (as shown in FIG. 9A-9B). In some implementations, the plurality of quantitative literacy metrics may be based on a fourth set of predetermined parameters. The fourth set of predetermined parameters may be at least one of numerical values, guidelines, upper boundaries, lower boundaries, or other evaluation criteria for each metric within the plurality of quantitative literacy metrics.

The fourth set of predetermined parameters may be stored in the assessment application 119, 219 on the reviewer computing device 103, 203 (as shown in FIGS. 1-2). The fourth set of predetermined parameters may be stored in the memory 121, 221 on the reviewer computing device 103, 203 (as shown in FIGS. 1-2). The fourth set of predetermined parameters may be stored in the assessment application 309 on the communication source computing device 301 (as shown in FIG. 3). The fourth set of predetermined parameters may be stored in the memory 311 on the communication source computing device 301 (as shown in FIG. 3). The fourth set of predetermined parameters may be stored in the form of a hard (paper) document or an electronic document (as shown in FIG. 4).

In some implementations, the assessment application 119, 219, 309 may transform the contents of the medical communication to fit within the fourth set of predetermined parameters. For example, the assessment application 119, 219, 309 may convert units of measurements from the metric system to the U.S. customary system.

The health literacy assessment may be provided to the communication source to facilitate an improved conveyance of at least one of the medical diagnostic information or the medical treatment information to increase comprehension by patients of all educational levels (505). The conveyance of the at least one of the medical diagnostic information or the medical treatment information may be improved through simplifying, organizing, or shortening the contents of the medical communication using the health literacy assessment.

In some implementations, a new medical communication based on the health literacy assessment may be received from the communication source (507). The new medical communication may contain at least one of medical diagnostic information or medical treatment information.

FIGS. 6A-6D show an example plurality of appearance metrics 600 according to an aspect of the present disclosure.

The plurality of appearance metrics 600 may be used by a reviewer who uses the assessment application 119, 219 on the reviewer computing device 103, 203 (as shown in FIGS. 1-2) to generate a health literacy assessment of the medical communication. The plurality of appearance metrics 600 may be used by the assessment application 119, 219 on the reviewer computing device 103, 203 (as shown in FIGS. 1-2) to generate a health literacy assessment of the medical communication. The plurality of appearance metrics 600 may be used by the assessment application 309 on the communication source computing device 301 (as shown in FIG. 3) to generate a health literacy assessment of the medical communication. The plurality of appearance metrics 600 may be used by a reviewer (as shown in FIG. 4) to generate a health literacy assessment of the medical communication.

FIG. 6A shows a first evaluation criteria 601 of the plurality of appearance metrics 600. The first evaluation criteria 601 includes metrics evaluating the spacing, contrast, and typography of the medical communication to make the information within the medical communication look easy to read by the patient. Each element within the first evaluation criteria 601 may be evaluated under the evaluation column (work needed) 603. An indication may be made that the medical communication needs much, some, none or little work needed for each metric under the first evaluation criteria 601. For example, a score 1-3 may indicate that much work is needed, a score of 4-7 may indicate that some work is needed, and a score of 8-10 may indicate that none or little work is needed. In other example, a score of D to F may indicate that much is needed, a score of B to C may indicate that some work is needed, and a score of A may indicate that none or little work is needed.

As shown, there are three options for the evaluation column 603, however any number or form of options may be used interchangeably according to various embodiments. For example, the evaluation column 603 may include a one to ten scale for each metric under the first evaluation criteria 601. In some embodiments, the evaluation column 603 may include notes for each metric under the first evaluation criteria 601 that addresses specific shortfalls of the medical communication.

The metrics under the first evaluation criteria 601 include paragraph depth and chunking of information metric 605, line length metric 607, amount of white space metric 609, font size metric 611, font style and case metric 613, line spacing metric 615, contrast metric 617, and background metric 619. The paragraph depth and chunking of information metric 605 evaluates the depth (paragraph length) as well as the grouping or chunking (paragraph grouping) of the medical communication. In some implementations, the paragraph length is evaluated based on a range of line length. For example, an ideal paragraph length may be between four and five lines of text. The grouping or chunking of the medical communication may evaluate the breaking up or dividing up of longer information into logical groups or chunks.

The line length metric 607 may evaluate the text based on a physical length. For example, the ideal length of the lines within the medical communication may be approximately five inches across. The amount of white space metric 609 may evaluate the amount of white space used in the medical communication to provide visual relief for the patient. The font size metric 611 may evaluate the font size used in the medical communication. For example, a font size of 12-point Times New Roman equivalent or larger may be necessary for patients who have poor vision. In another example, a score of 1-3 or D to F for the font size metric 611 may be given for the use 6-point font within the medical communication.

The font style and case metric 613 may evaluate the medical communication based on additional criteria. For a hard (paper) copy of the medical communication, the font style and case metric 613 may evaluate the use of either serif or sans serif font. For a web (electronic) copy of the medical communication, the font style and case metric 613 may evaluate the use of sans serif. In some implementations, the font style and case metric 613 may evaluate the use or limited use of at least one of reverse type, italics, all caps, or the number of fonts used.

The line spacing (leading) metric 615 may evaluate the medical communication based on the spacing of each line within the medical communication. For example, the ideal line spacing may be 1.5. The contrast metric 617 may evaluate the contrast between the background the text of the medical communication. For example, black text and white background may be preferred to dark grey and white background. The background metric 619 may evaluate the medical communication based on the presence of at least one of ghosting or superimposition. Ghosting being the presence of text placed on top of shaded backgrounds, photos or patterns. Superimposition being the presence of text on top of illustrations.

FIG. 6B shows a second evaluation criteria 621 of the plurality of appearance metrics 600. The second evaluation criteria 621 includes metrics evaluating the organization and layout of the medical communication to make the information within the medical communication easy to find and follow by the patient. Each element within the second evaluation criteria 621 may be evaluated under the evaluation column (work needed) 603. An indication may be made that the medical communication needs much, some, none or little work needed for each metric under the second evaluation criteria 621. For example, a score 1-3 may indicate that much work is needed, a score of 4-7 may indicate that some work is needed, and a score of 8-10 may indicate that none or little work is needed. In other example, a score of D to F may indicate that much is needed, a score of B to C may indicate that some work is needed, and a score of A may indicate that none or little work is needed.

As shown, there are three options for the evaluation column 603, however any number or form of options may be used interchangeably according to various embodiments. For example, the evaluation column 603 may include a one to ten scale for each metric under the second evaluation criteria 621. In some embodiments, the evaluation column 603 may include notes for each metric under the second evaluation criteria 621 that addresses specific shortfalls of the medical communication.

The metrics under the second evaluation criteria 621 include headings, subheadings, and short titles metric 623, vertical lists with bullets, letters, and numbers metric 625, indentation metric 627, margins and alignment metric 629, and boxing and callouts metric 631. The headings, subheadings, and short title metric 623 may evaluate the presence of headings, subheadings, and short titles. In some implementations, the presence of headings, subheadings, and short titles may be evaluated based on the use of bolded or enlarged headings and subheadings to highlight the key messages and make information easy to find and follow by the patient. The presence of headings, subheadings, and short titles may be evaluated based on the use of a short sentence, a phrase, or a single word. For example, the heading "You have Diabetes" may be given a score of 8-10 or A for the headings, subheadings, and short title metric 623.

The vertical lists with bullets, letters, and numbers metric 625 may evaluate the usage of breaking dense text into vertical lists to limits concept density and to make information easier to find. The vertical lists with bullets, letters, and numbers metric 625 may limit the number of items or concepts to no more than seven. However, other numerical values for the limit of the number of items or concepts may be used interchangeably according to various embodiments.

The vertical lists with bullets, letters, and numbers metric 625 may evaluate the breaking of longer lists into logical groups or chunks to avoid overwhelming the reader (patient). The vertical lists with bullets, letters, and numbers metric 625 may evaluate the use of listing items using parallel structure (e.g. the same grammatical form). For example, the parallel structure may be the use of all verbs or all nouns. The vertical lists with bullets, letters, and numbers metric 625 may evaluate the usage of alphabetical order when items or topics are of equal importance. The vertical lists with bullets, letters, and numbers metric 625 may evaluate the use of numbers when items or steps need to be presented in a particular sequence. The vertical lists with bullets, letters, and numbers metric 625 may allow the use of a single bullet within a larger list to provide consistency when only one point is being made.

The indentation metric 627 may evaluate the use of indentation to visually call attention to sub-points. The margins and alignment metric 629 may evaluate the usage of a left justified margin to show a reader (patient) where to begin. The margins and alignment metric 629 may evaluate the usage of a ragged right margin to help readers (patients) find and keep their place from one line to the next. The margins and alignment metric 629 may evaluate the avoidance of full justification to eliminate potentially confusing gaps. The margins and alignment metric 629 may evaluate the usage of centering for only short blocks of text when necessary. The boxing and callouts metric 631 may evaluate the usage of boxing, when needed, to draw attention to key messages.

FIG. 6C shows a continuation of the second evaluation criteria 621 of the plurality of appearance metrics 600. The second evaluation criteria 621 includes metrics evaluating uninterrupted copy and wrapping of text (uninterrupted text) metric 633, usage of a table of contents metric 635, numbering of pages metric 637, section indicators metric 639, and color coding metric 641.

The uninterrupted text metric 633 may evaluate the usage of uninterrupted text in order to ensure that readers are kept from having to follow a word, a sentence, or a message from one column to the next, or from one page to the next. The uninterrupted text metric 633 may evaluate the usage of keeping similar information on the same page or on a two-page spread whenever possible. The uninterrupted text metric 633 may evaluate the avoidance of end-of-line hyphens. The uninterrupted text metric 633 may evaluate the absence of widows, orphans, and misfits. The uninterrupted text metric 633 may evaluate the avoidance of wrapped text.

The usage of a table of contents metric 635 may evaluate the usage of keeping titles in the tables of contents short and immediately informative as well as matching them with the headers on the pages that follow. The usage of a table of contents metric 635 may evaluate the usage of usable information to guide the reader. The usage of a table of contents metric 635 may evaluate the organization of the table of contents into categories or chunks, with bolded headers and sub-headers, when the table of contents is lengthy.

The numbering of pages metric 637 evaluates the usage of page numbers to guide the reader and help providers to counsel consumers. The numbering of pages metric 637 may evaluate the usage of labels on page bottoms that serve as advance organizer when the document (medical communication) is lengthy. For example, the usage of labels on page bottoms may be used when the document is 12 or more pages in length.

The section indicators metric 639 may evaluate the usage of clear section headers or parts for longer documents. The color coding metric 641 may evaluate the usage of color coding to ensure the color coding is done in a consistent and non-confusing way.

FIG. 6D shows a third evaluation criteria 643 of the plurality of appearance metrics 600. The third evaluation criteria 643 includes metrics evaluating the graphics and illustrations to make the information look interesting and clear. Each element within the third evaluation criteria 643 may be evaluated under the evaluation column (work needed) 603. An indication may be made that the medical communication needs much, some, none or little work needed for each metric under the third evaluation criteria 643. For example, a score 1-3 may indicate that much work is needed, a score of 4-7 may indicate that some work is needed, and a score of 8-10 may indicate that none or little work is needed. In other example, a score of D to F may indicate that much is needed, a score of B to C may indicate that some work is needed, and a score of A may indicate that none or little work is needed.

As shown, there are three options for the evaluation column 603, however any number or form of options may be used interchangeably according to various embodiments. For example, the evaluation column 603 may include a one to ten scale for each metric under the third evaluation criteria 643. In some embodiments, the evaluation column 603 may include notes for each metric under the third evaluation criteria 643 that addresses specific shortfalls of the medical communication.

The metrics under the third evaluation criteria 643 include graphic usefulness (usage of graphics) metric 645, usage of realistic graphics metric 647, clarity and simplicity of graphics metric 649, usage of anatomical illustrations and microscopic views metric 651, captions and cueing metric 653, and depiction of unwanted behaviors metric 655. The usage of graphics metric 645 may evaluate the usage of graphics that contribute to the message (medical communication). The contributions to the message may include at least one of attracting attention, indicating who the material is for, increasing comprehension of the text, support of the main messages, or motivation or inspiration for the reader to take the intended action.

The usage of realistic graphics metric 647 may evaluate the usage of realistic graphics that would indicate what the information is about, even in the absence of the relevant copy and even to people who may not be familiar with the topic. The clarity and simplicity of graphics metric 649 may evaluate the usage of illustrations that are readily recognizable. The clarity and simplicity of graphics metric 649 may evaluate the usage of unnecessary background or extraneous details. The clarity and simplicity of graphics metric 649 may evaluate the usage of graphics next to the related copy.

The usage of anatomical illustrations and microscopic views metric 651 may evaluate the usage of any internal parts of the body in context of the rest of the body. The usage of anatomical illustrations and microscopic views metric 651 may evaluate the avoidance or the careful explanation of any microscopic views used in the medical communication.

The captions and cueing metric 653 may evaluate the usage of captions that clarify the main point of a graphic used in the medical communication. The captions and cueing metric 653 may evaluate the usage of explicit directional cues to call attention to parts of a graphic. For example, arrows or other generally recognized symbols used with brief captions in the medical communication may be evaluated. The depiction of unwanted behaviors metric 655 may evaluate the avoidance of inadvertently promoting unwanted behaviors.

FIGS. 7A-7F show an example plurality of readability metrics 700 according to an aspect of the present disclosure.

The plurality of readability metrics 700 may be used by a reviewer who uses the assessment application 119, 219 on the reviewer computing device 103, 203 (as shown in FIGS. 1-2) to generate a health literacy assessment of the medical communication. The plurality of readability metrics 700 may be used by the assessment application 119, 219 on the reviewer computing device 103, 203 (as shown in FIGS. 1-2) to generate a health literacy assessment of the medical communication. The plurality of readability metrics 700 may be used by the assessment application 309 on the communication source computing device 301 (as shown in FIG. 3) to generate a health literacy assessment of the medical communication. The plurality of readability metrics 700 may be used by a reviewer (as shown in FIG. 4) to generate a health literacy assessment of the medical communication.

FIG. 7A shows a first evaluation criteria 701 of the plurality of readability metrics 700. The first evaluation criteria 701 includes metrics evaluating the text of the medical communication to make the information easy to read by the patient. Each element within the first evaluation criteria 701 may be evaluated under the evaluation column (work needed) 703. An indication may be made that the medical communication needs much, some, none or little work needed for each metric under the first evaluation criteria 701. For example, a score 1-3 may indicate that much work is needed, a score of 4-7 may indicate that some work is needed, and a score of 8-10 may indicate that none or little work is needed. In other example, a score of D to F may indicate that much is needed, a score of B to C may indicate that some work is needed, and a score of A may indicate that none or little work is needed.

As shown, there are three options for the evaluation column 703, however any number or form of options may be used interchangeably according to various embodiments. For example, the evaluation column 703 may include a one to ten scale for each metric under the first evaluation criteria 701. In some embodiments, the evaluation column 703 may include notes for each metric under the first evaluation criteria 701 that addresses specific shortfalls of the medical communication.

The metrics under the first evaluation criteria 701 include document length and complexity (length and complexity) metric 705, word length metric 707, usage of word pronunciation guides metric 709, sentence length metric 711, and reading level metric 713. The document length and complexity metric 705 may a first prong for shorter documents a second prong for longer documents. For example, in some implementations the first prong may be for documents (medical communications) one to six pages in length and the second prong may be for documents greater than six pages in length. However, other page lengths may be used interchangeably according to various embodiments. The first prong of the document length and complexity metric 705 may evaluate the content for simplicity. The first prong of the document length and complexity metric 705 may evaluate the omission of "nice-to know" details and evaluate the inclusion of "need-to-know information." The second prong of the document length and complexity metric 705 may evaluate the inclusion of "nice-to-know information" when necessary.

The word length metric 707 may evaluate the use of shorter words when appropriate. For example, the word length metric 707 may evaluate the use of words that are three syllables or less in the medical communication. For example, a score of 1-3 or D to F for the word length metric 707 may be given for the use of the word "mesothelioma" within the medical communication. The usage of word pronunciation guides metric 709 may evaluate the use of pronunciation guides in the medical communication when needed. The sentence length metric 711 may evaluate the usage of short sentences. For example, the sentence length metric 711 may evaluate the medical communication for sentences that are ten to fifteen words or less in length. However, other word lengths may be used interchangeably according to various embodiments. The sentence length metric 711 may evaluate the use of varying sentence length to create an engaging rhythm and maintain attention of the reader.

The reading level metric 713 may be used to evaluate the reading level of the medical communication. For example, the reading level metric 713 may evaluate the medical communication for an ideal reading level of between fourth and sixth grade. However, other reading levels may be used interchangeably according to various embodiments. The reading level may be chosen to ensure understandability of the medical communication by marginal readers without making the information inaccurate, confusing, or making the flow of information seem choppy or childish.

FIG. 7B shows a continuation of the first evaluation criteria 701 of the plurality of readability metrics 700. The first evaluation criteria 701 includes clarity of purpose metric 715, usage of background information metric 717, sequence of information metric 719, usage of informative and scannable headers metric 721, usage of directives and call to action metric 723, usage of active voice for statements metric 725, and presence of abbreviations, acronyms, phone words, and symbols metric 727.

The clarity of purpose metric 715 may evaluate the inclusion of a useful title and introductory text that makes it clear what the material (content of the medical communication) is about. The usage of background information metric 717 may evaluate the inclusion of background information, when needed, to help a lay reader (patient) to better grasp the information being presented. The sequence of information metric 719 may evaluate the consideration of the priorities of the reader and the presentation of information in an order that is likely to make sense to the reader.

The usage of informative and scannable headers metric 721 may evaluate the use of descriptive headers and subheaders to break the information within the medical communication into manageable sections that can be easily understood and scanned for the main messages. The usage of directives or calls to action metric 723 may evaluate the medical communication for clear, explicit, and not implied calls to action. The usage of directives or calls to action metric 723 may evaluate the usage of verbs at the beginning of the directives or calls to action. The usage of directives or calls to action metric 723 may evaluate the medical communication for how direct the directives or calls to action are presented. For example, the medical communication may be evaluated for quickly getting to the point and telling the patient what to do if they want to achieve a specific desired result. The usage of directives or calls to action metric 723 may evaluate the usage of key calls to action being placed first in the medical communication. For example, the medical communication may be evaluated for the omission of calls to action in embedded deep in the document and the inclusion of calls to action at the beginning of the document.

The usage of active voice for statements metric 725 may evaluate the use of active voice for statements within the medical communication whenever possible. For example, the statement "we made an error" may be preferred over "an error was made." The presence of abbreviations, acronyms, phone words, and symbols metric 727 may evaluate the medical communication for the omission of acronyms, abbreviations, and symbols. In some implementations, the presence of abbreviations, acronyms, phone words, and symbols metric 727 may evaluate the medical communication for the inclusion of explanations of the abbreviations, acronyms, phone words, and symbols. The presence of abbreviations, acronyms, phone words, and symbols metric 727 may evaluate the presence of accompanying numerals when phone words are present in the medical communication.

FIG. 7C shows a second evaluation criteria 729 of the plurality of readability metrics 700. The second evaluation criteria 729 includes metrics evaluating the text of the medical communication to make the information within the medical communication easy to understand by the patient. The second evaluation criteria 729 includes word clarity metric 731 and usage of glossaries metric 733. Each element within the second evaluation criteria 729 may be evaluated under the evaluation column (work needed) 703. An indication may be made that the medical communication needs much, some, none or little work needed for each metric under the second evaluation criteria 729. For example, a score 1-3 may indicate that much work is needed, a score of 4-7 may indicate that some work is needed, and a score of 8-10 may indicate that none or little work is needed. In other example, a score of D to F may indicate that much is needed, a score of B to C may indicate that some work is needed, and a score of A may indicate that none or little work is needed.

As shown, there are three options for the evaluation column 703, however any number or form of options may be used interchangeably according to various embodiments. For example, the evaluation column 703 may include a one to ten scale for each metric under the second evaluation criteria 729. In some embodiments, the evaluation column 703 may include notes for each metric under the second evaluation criteria 729 that addresses specific shortfalls of the medical communication.

The word clarity metric 731 may evaluate the omission of words likely to cause confusion. In some implementations, the word clarity metric 731 may evaluate the inclusion of explanations of the meanings of words likely to cause confusion. Words likely to cause confusion may include professional jargon (e.g. renal vs. kidney), value judgment words (e.g. a lot of rest vs. eight hours of sleep), category words (e.g. poultry vs. chicken), concepts words (e.g. self-esteem vs. the way you feel about yourself), and idioms (e.g. feel under the weather vs. don't feel well). Professional jargon may include terminology used in the medical, legal, social service, or insurance setting. For example, a score of 1-3 or D to F for the word clarity metric may be given for the use of "hallux" within the medical communication.

The word clarity metric 731 may evaluate the usage of a familiar term as the lead. In some implementations the technical term may be made into a parenthetical when needed. For example, if the medical communication mentions sodium, the familiar term "salt" may be used as the lead with "sodium" used in parentheses such as: salt (sodium). The word clarity metric 731 may evaluate the use of different terms with the same meaning within the medical communication to avoid potential confusion. For example, Affordable Care Act, ACA, or Obamacare. The word clarity metric 731 may evaluate the usage of a word or term consistently throughout the document (medical communication).

The usage of glossaries metric 733 may evaluate the usage of an easy-to-read glossary when needed. In some implementations, the glossary may be used to define or explain technical or medical terms whenever such terms appear in the medical communication. The usage of glossaries metric 733 may evaluate to ensure the definitions within the glossary are kept simple and may test them with marginal readers in the intended audience. The usage of glossaries metric 733 may evaluate the presence of explanations, in addition to the definitions, to assist with making implied messages explicit for readers who are unfamiliar with a term and the issues that surround it.

FIG. 7D shows a continuation of the second evaluation criteria 729 of the plurality of readability metrics 700. The second evaluation criteria 729 includes presence of answers to questions metric 735, usage of parallel construction for contrasting and comparing metric 737, usage of cross-referencing metric 739, and usage of summaries and review metric 741.

The presence of answers to questions metric 735 may evaluate the answer to any question posed to ensure that it is answered promptly and clearly before any additional detail is disclosed. The usage of parallel construction for contrasting and comparing metric 737 may evaluate the usage of parallel construction (repeated wording and layout) whenever there is a need to easily contrast and compare at least two sections of information within the medical communication. For example, parallel construction may be used to compare different health plans for the patient to choose.

The usage of cross-referencing metric 739 may evaluate the limited usage of cross-referencing in order to limit the need for the reader to search around for related information. The usage of summaries and review metric 741 may evaluate summaries to ensure that key points are summarizes and reviews are offered for new information or for long documents.

FIG. 7E shows a third evaluation criteria 743 of the plurality of readability metrics 700. The third evaluation criteria 743 includes metrics evaluating the text of the medical communication to ensure that the information in the medical communication is easy to relate to. Each element within the third evaluation criteria 743 may be evaluated under the evaluation column (work needed) 703. An indication may be made that the medical communication needs much, some, none or little work needed for each metric under the third evaluation criteria 743. For example, a score 1-3 may indicate that much work is needed, a score of 4-7 may indicate that some work is needed, and a score of 8-10 may indicate that none or little work is needed. In other example, a score of D to F may indicate that much is needed, a score of B to C may indicate that some work is needed, and a score of A may indicate that none or little work is needed.

As shown, there are three options for the evaluation column 703, however any number or form of options may be used interchangeably according to various embodiments. For example, the evaluation column 703 may include a one to ten scale for each metric under the third evaluation criteria 743. In some embodiments, the evaluation column 703 may include notes for each metric under the third evaluation criteria 743 that addresses specific shortfalls of the medical communication.

The metrics under the third evaluation criteria 743 include usage of reader-focused content and reader appeal metric 745, usage of conversational style metric 747, usage of a narrative approach metric 749, and presence of an opportunity for interaction metric 751. The reader-focused content and reader appeal metric 745 may evaluate the addressing of key concerns and interest of the lay readership (patient). The reader-focused content and reader appeal metric 745 may evaluate the addressing of information on a way that intended readers (patients) will perceive the materials (medical communication). For example, intended reader may perceive the materials as being at least one interesting, important, needed, timely, practical (easy to respond to), acceptable (not offensive in any way), believable, persuasive, or personally relevant (meant especially for them).

The usage of conversational style metric 747 may evaluate the addressing of the reader directly. For example, the medical communication may state "your heart" vs. "the heart." The usage of conversational style metric 747 may evaluate the usage of familiar terms and the active voice such as "living room language."

The usage of a narrative approach metric 749 may evaluate the use of one or more techniques to make the information within the medical communication easier to engage with, believe, accepts, or relate to as being personally relevant to the reader. In some implementations, the one or more techniques may include culturally sensitive and non-stigmatizing storylines, dialogues, testimonials, or quotes.

The presence of an opportunity for interaction metric 751 may evaluate the usage of one or more approaches to invite interaction or engagement with the reader (patient) with the medical communication and encourage deeper thought on the part of the reader. In some implementations, the one or more approaches may include a helpful checklist, a brief but relevant quiz, questions and answers about misconceptions or controversies, or fill in the blank.

FIG. 7F shows a fourth evaluation criteria 753 of the plurality of readability metrics 700. The fourth evaluation criteria 753 includes metrics evaluating the breaking of selected grammar and style rules in order to make information easier to read and understand by the patient. Each element within the fourth evaluation criteria 753 may be evaluated under the evaluation column (work needed) 703. An indication may be made that the medical communication needs much, some, none or little work needed for each metric under the fourth evaluation criteria 753. For example, a score 1-3 may indicate that much work is needed, a score of 4-7 may indicate that some work is needed, and a score of 8-10 may indicate that none or little work is needed. In other example, a score of D to F may indicate that much is needed, a score of B to C may indicate that some work is needed, and a score of A may indicate that none or little work is needed.

As shown, there are three options for the evaluation column 703, however any number or form of options may be used interchangeably according to various embodiments. For example, the evaluation column 703 may include a one to ten scale for each metric under the fourth evaluation criteria 753. In some embodiments, the evaluation column 703 may include notes for each metric under the fourth evaluation criteria 753 that addresses specific shortfalls of the medical communication.

The metrics under the fourth evaluation criteria 753 include usage of conjunctions at the beginning of sentences metric 755, usage of prepositions at the end of sentences metric 757, usage of an Oxford comma metric 759, and usage of numerals for numbers metric 761. The usage of conjunctions at the beginning of sentences metric 755 may evaluate the use, when needed, of a conjunction at the beginning of sentences to shorten sentences and to maintain a conversational tone. The usage of prepositions at the end of sentences metric 757 may evaluate the use, when needed, of a preposition at the end of sentences to make sentences easier to understand by the patient and maintain a conversational tone.

The usage of an oxford comma (usage of a serial comma) metric 759 may evaluate the use of a comma before a conjunction when the conjunction joins the last two elements in a series of three or more in order to help prevent ambiguity. The usage of numerals for numbers metric 761 may evaluate the use of numerals instead of words to make them easier to spot and grasp by the patient in the body of the text. The usage of numerals for numbers metric 761 may evaluate the use of numerals instead of or in addition to words when the number is likely to be important to the patient. For example, the text of the medical communication may include a statement such as "send this form back within ten (10) days."

FIGS. 8A-8B show an example plurality of document literacy metrics 800 according to an aspect of the present disclosure.

The plurality of document literacy metrics 800 may be used by a reviewer who uses the assessment application 119, 219 on the reviewer computing device 103, 203 (as shown in FIGS. 1-2) to generate a health literacy assessment of the medical communication. The plurality of document literacy metrics 800 may be used by the assessment application 119, 219 on the reviewer computing device 103, 203 (as shown in FIGS. 1-2) to generate a health literacy assessment of the medical communication. The plurality of document literacy metrics 800 may be used by the assessment application 309 on the communication source computing device 301 (as shown in FIG. 3) to generate a health literacy assessment of the medical communication. The plurality of document literacy metrics 800 may be used by a reviewer (as shown in FIG. 4) to generate a health literacy assessment of the medical communication.

FIG. 8A shows an evaluation criterion 801 of the plurality of document literacy metrics 800. The evaluation criterion 801 includes metrics evaluating the document literacy of the of the medical communication to make non-continuous text easy to understand by the patient. Each element within the evaluation criterion 801 may be evaluated under the evaluation column (work needed) 803. An indication may be made that the medical communication needs much, some, none or little work needed for each metric under the evaluation criterion 801. For example, a score 1-3 may indicate that much work is needed, a score of 4-7 may indicate that some work is needed, and a score of 8-10 may indicate that none or little work is needed. In other example, a score of D to F may indicate that much is needed, a score of B to C may indicate that some work is needed, and a score of A may indicate that none or little work is needed.

As shown, there are three options for the evaluation column 803, however any number or form of options may be used interchangeably according to various embodiments. For example, the evaluation column 803 may include a one to ten scale for each metric under the evaluation criterion 801. In some embodiments, the evaluation 803 may include notes for each metric under the evaluation criterion 801 that addresses specific shortfalls of the medical communication.

The metrics under the evaluation criterion 801 include usage of forms and diaries metric 805 and usage of charts and tables metric 807. The usage of forms and diaries metric 805 may have a first prong for the introduction and a second prong for the body. The first prong of the usage of forms and diaries metric 805 may evaluate the presence of a purpose in the introduction that explains, to the patient, why the document (medical communication) is important and what to do with it. The first prong the usage of forms and diaries metric 805 may evaluate the presence of directions to the patient that provides clear and easily understood directions for the patient to follow. The first prong of the usage of forms and diaries metric 805 may evaluate the presence of sample entries for the patient.

The second prong of the usage of forms and diaries metric 805 may evaluate the font size to ensure a large enough font size is used for the patient to easily read the medical communication. The second prong of the usage of forms and diaries metric 805 may evaluate the number of entries in the document (medical communication) to ensure that for a simple document only a limited number of entries is used. The second prong of the usage of forms and diaries metric 805 may evaluate the usage of shading or white space in the medical communication to distinguish one line or section from the next. The second prong of the usage of forms and dairies metric 805 may evaluate the quantity of text within the medical communication to limit the amount of writing within the medical communication.

The charts and tables metric 807 may evaluate the use and number of columns to keep a chart simple and easy to follow. For example, a score of 1-3 or D-F for the charts and tables metric 807 may be given for the use of 100 columns for the chart. The charts and tables metric 807 may evaluate the use of labels to provide an explicit indication of what each column or row (axis) means. The chart and tables metric 807 may evaluate the use of arrows, when needed, to indicate to the patient how to navigate the x-y axis orientation of the table. The chart and tables metric 807 may evaluate the quantity of text to limit the amount of writing within the chart and/or table in the medical communication. The chart and tables metric 807 may evaluate the use of color coding or light shading to distinguish one row or column from the other.

FIG. 8B shows a continuation of the evaluation criterion 801 of the plurality of document literacy metrics 800. The evaluation criterion 801 includes usage of graphs metric 809 and usage of maps metric 811. The usage of graphs metric 809 may evaluate the interpretation of information for lay readers (e.g. the patient). The usage of graphs metric 809 may evaluate the usage of laymen's terms for the description of the elements and various interpretations of the data within the graph(s).

The usage of maps metric 811 may evaluate the design issues within one or more maps that make information easy to see and read. The design issues may include adequate font type, adequate font size, and adequate contrast. The usage of maps metric 811 may evaluate the map-related issues to ensure the map is easy to follow. The map-related issues may include a placement of a map key, inclusion of a North-South-East-West orientation, symbols (e.g. male and female restroom icons), arrows to indicate directions and destinations, and color coding. The usage of maps metric 811 may evaluate the inclusion of offers of information as to whom to contact for verbal guidance.

FIGS. 9A-9B show an example plurality of quantitative literacy metrics 900 according to an aspect of the present disclosure.

The plurality of quantitative literacy metrics 900 may be used by a reviewer who uses the assessment application 119, 219 on the reviewer computing device 103, 203 (as shown in FIGS. 1-2) to generate a health literacy assessment of the medical communication. The plurality of quantitative literacy metrics 900 may be used by the assessment application 119, 219 on the reviewer computing device 103, 203 (as shown in FIGS. 1-2) to generate a health literacy assessment of the medical communication. The plurality of quantitative literacy metrics 900 may be used by the assessment application 309 on the communication source computing device 301 (as shown in FIG. 3) to generate a health literacy assessment of the medical communication. The plurality of quantitative literacy metrics 900 may be used by a reviewer (as shown in FIG. 4) to generate a health literacy assessment of the medical communication.

FIG. 9A shows a first evaluation criteria 901 of the plurality of quantitative literacy metrics 900. The first evaluation criteria 901 includes metrics evaluating the quantitative literacy of the medical communication to make the numbers within the medical communication meaningful to the patient. Each element within the first evaluation criteria 901 may be evaluated under the evaluation column (work needed) 903. An indication may be made that the medical communication needs much, some, none or little work needed for each metric under the first evaluation criteria 901. For example, a score 1-3 may indicate that much work is needed, a score of 4-7 may indicate that some work is needed, and a score of 8-10 may indicate that none or little work is needed. In other example, a score of D to F may indicate that much is needed, a score of B to C may indicate that some work is needed, and a score of A may indicate that none or little work is needed.

As shown, there are three options for the evaluation column 903, however any number or form of options may be used interchangeably according to various embodiments. For example, the evaluation column 903 may include a one to ten scale for each metric under the first evaluation criteria 901. In some embodiments, the evaluation column 903 may include notes for each metric under the first evaluation criteria 901 that addresses specific shortfalls of the medical communication.

The metrics under the first evaluation criteria 901 may include usage of numbers metric 905, usage of plain language explanations metric 907, usage of calculations metric 909, usage of visuals metric 911, and usage of analogies and comparisons metric 913. The usage of numbers metric 905 may evaluate the limited use of numbers in the medical communication. The usage of numbers metric 905 may evaluate the usage of numbers when precision is needed (e.g. blood sugar, dose of medicine). For example, the statement "take several pills daily of your prescribed medication" may be given a score of 1-3 or D to F for the usage of numbers metric 905.

The usage of plain language explanations metric 907 may evaluate the usage of explanations to the meaning of specific numbers with everyday words within the medical communication. For example, the medical communication could describe 49 percent as about half for better understanding by the layperson (patient). The usage of calculations metric 909 may evaluate the inclusion of mathematical calculations performed for the patient whenever possible. In some implementations, the usage of calculations metric 909 may evaluate the inclusion of sample calculations whenever patient-specific calculations are not possible.

The usage of visuals metric 911 may evaluate the inclusion of pictures within the medical communication that help explain numerical concepts whenever needed. The usage of analogies and comparisons metric 913 may evaluate the use of analogies and comparisons to familiar object to help convey quantitative information to the patient.

FIG. 9B shows a second evaluation criteria 915 of the plurality of quantitative literacy metrics 900. Each element within the second evaluation criteria 915 may be evaluated under the evaluation column (work needed) 903. An indication may be made that the medical communication needs much, some, none or little work needed for each metric under the second evaluation criteria 915. For example, a score 1-3 may indicate that much work is needed, a score of 4-7 may indicate that some work is needed, and a score of 8-10 may indicate that none or little work is needed. In other example, a score of D to F may indicate that much is needed, a score of B to C may indicate that some work is needed, and a score of A may indicate that none or little work is needed.

As shown, there are three options for the evaluation column 903, however any number or form of options may be used interchangeably according to various embodiments. For example, the evaluation column 903 may include a one to ten scale for each metric under the second evaluation criteria 915. In some embodiments, the evaluation column 903 may include notes for each metric under the second evaluation criteria 915 that addresses specific shortfalls of the medical communication.

The metrics under the second evaluation criteria 915 may include usage of estimates metric 917, usage of frequencies metric 919, usage of measurement systems metric 921, framing of outcomes metric 923, and consistency when making comparisons metric 925. The usage of estimates metric 917 may evaluate the inclusion of estimates numbers in order to provide additional information to the patient.

The usage of frequencies metric 919 may evaluate the inclusion of frequencies instead of decimals or percentages. For example, instead of 1% or 0.01 the medical communication may state one in a hundred or one out of a hundred. The usage of measurement systems metric 921 may evaluate the inclusion of a measurement system that the reader (patient) uses or is accustomed to. For example, if the patient is from the United States the medical communication may use the U.S. Customary System. In another example, if the patient is from Europe the medical communication may use the metric system. In another example, a score of 1-3 or D to F for the measurement system metric 921 may be given for the use of the metric system when the patient has indicated that they use the U.S. Customary System.

The framing of outcomes metric 923 may evaluate the presence of stated outcomes phrased in both positive and negative terms. The consistency when making comparisons metric 925 may evaluate the presence of consistent usage of denominators and timeframe when comparisons are made.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of systems, apparatuses, and methods as disclosed herein, which is defined solely by the claims. Accordingly, the systems, apparatuses, and methods are not limited to that precisely as shown and described.

Certain embodiments of systems, apparatuses, and methods are described herein, including the best mode known to the inventors for carrying out the same. Of course, variations on these described embodiments will become apparent to those of ordinary skill in the art upon reading the foregoing description. The inventor expects skilled artisans to employ such variations as appropriate, and the inventors intend for the systems, apparatuses, and methods to be practiced otherwise than specifically described herein. Accordingly, the systems, apparatuses, and methods include all modifications and equivalents of the subject matter recited in the claims appended hereto as permitted by applicable law. Moreover, any combination of the above-described embodiments in all possible variations thereof is encompassed by the systems, apparatuses, and methods unless otherwise indicated herein or otherwise clearly contradicted by context.

Groupings of alternative embodiments, elements, or steps of the systems, apparatuses, and methods are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses an approximation that may vary, yet is capable of performing the desired operation or process discussed herein.

The terms "a," "an," "the" and similar referents used in the context of describing the systems, apparatuses, and methods (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the systems, apparatuses, and methods and does not pose a limitation on the scope of the systems, apparatuses, and methods otherwise claimed. No language in the present specification should be construed as indicating any non-claimed element essential to the practice of the systems, apparatuses, and methods.

All patents, patent publications, and other publications referenced and identified in the present specification are individually and expressly incorporated herein by reference in their entirety for the purpose of describing and disclosing, for example, the compositions and methodologies described in such publications that might be used in connection with the systems, apparatuses, and methods. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method for improving health literacy of patient materials comprising:
   receiving, from a communication source, a medical communication created by a medical professional for a patient containing at least one of medical diagnostic information or medical treatment information;
   performing an analysis of the received medical communication using multiple metrics including at least one of a plurality of appearance metrics, a plurality of readability metrics, a plurality of document literacy metrics, or a plurality of quantitative literacy metrics;
   generating a health literacy assessment of the medical communication based on the analysis of the received medical communication and indicating a level of understandability of the medical communication; and
   providing the health literacy assessment to the communication source to facilitate an improved conveyance of the at least one of the medical diagnostic information or the medical treatment information.

2. The method of claim 1, wherein the health literacy assessment includes a grading for each of the multiple metrics used in the analysis.

3. The method of claim 1, wherein the health literacy assessment includes a grading of the level of understandability of the medical communication, and at least one suggestion for improving the grading.

4. The method of claim 1, wherein the health literacy assessment includes a grading of the level of understandability of the medical communication, and at least one explanation for the grading.

5. The method of claim 1, wherein the multiple metrics include at least two of:
   at least one of the plurality of appearance metrics;
   at least one of the plurality of readability metrics;
   at least one of the plurality of document literacy metrics; or
   at least one of the plurality of quantitative literacy metrics.

6. The method of claim 1, further comprising at least one of revising at least a portion of the medical communication or creating a new version of the medical communication to increase the level of understandability of the medical communication based on the health literacy assessment.

7. An apparatus for improving health literacy of patient materials comprising:
   a memory configured to store an assessment application corresponding to a reviewer;
   a network access device configured to receive a medical communication, from a communication source, containing at least one of medical diagnostic information or medical treatment information and being created by a medical professional;
   one or more processors configured to perform operations of the assessment application, the operations comprising:
      performing an analysis of the received medical communication using multiple metrics including at least one of a plurality of appearance metrics, a plurality of readability metrics, a plurality of document literacy metrics, or a plurality of quantitative literacy metrics, and
      generating a health literacy assessment of the medical communication based on the analysis of the received medical communication and indicating a level of understandability of the medical communication; and
   an output device configured to output the health literacy assessment to facilitate an improved conveyance of the at least one of the medical diagnostic information or the medical treatment information.

8. The apparatus of claim 7, wherein the output device includes a user interface.

9. The apparatus of claim 8, wherein the network access device receives the medical communication from an apparatus corresponding to the communication source.

10. The apparatus of claim 9, wherein the operations further comprise generating a new medical communication based on the health literacy assessment and containing the at least one of medical diagnostic information or medical treatment information, the new medical communication being generated to have an improved level of understandability.

11. The apparatus of claim 9, wherein the health literacy assessment includes a grading of the level of understandability of the medical communication, and at least one suggestion for improving the grading.

12. A method for generating a score for patient materials to improve health literacy comprising:
    storing, in a memory, an assessment application;
    receiving, from a network access device or an input device, a medical communication created by a medical professional and containing at least one of medical diagnostic information or medical treatment information;
    analyzing, using one or more processor and the assessment application, the received medical communication using multiple metrics including at least one of a plurality of appearance metrics, a plurality of readability metrics, a plurality of document literacy metrics, or a plurality of quantitative literacy metrics;
    generating, using the one or more processors and the assessment application and based on the analysis of the received medical communication, a health literacy score of the medical communication that indicates ease of understandability of the received medical communication; and
    outputting, using an output device, the health literacy score to facilitate an improved conveyance of the at least one of the medical diagnostic information or the medical treatment information.

13. The method of claim 12, wherein the output device includes a user interface.

14. The method of claim 13, wherein the network access device receives the medical communication from an apparatus corresponding to a communication source.

15. The method of claim 12, further comprising generating, using the one or more processors, a new medical communication based on the health literacy score and containing the at least one of medical diagnostic information or medical treatment information, the new medical communication being generated to have an improved level of understandability.

16. The method of claim 12, wherein the health literacy score includes a grading for each of the multiple metrics used in the analysis.

17. The method of claim 12, wherein the health literacy score includes a grading of the ease of understandability of the medical communication, and at least one suggestion for improving the grading.

18. The method of claim 12, wherein the health literacy score includes a grading of the ease of understandability of the medical communication, and at least one explanation for the grading.

19. The method of claim 12, wherein the multiple metrics include at least two of:
- at least one of the plurality of appearance metrics,
- at least one of the plurality of readability metrics;
- at least one of the plurality of document literacy metrics; or
- at least one of the plurality of quantitative literacy metrics.

20. The method of claim 12, further comprising at least one of revising at least a portion of the medical communication or creating a new version of the medical communication, using the one or more processor and the assessment application, to increase the ease of understandability of the medical communication based on the health literacy score.

* * * * *